US008268988B2

(12) United States Patent
Zablocki et al.

(10) Patent No.: US 8,268,988 B2
(45) Date of Patent: *Sep. 18, 2012

(54) PROCESS FOR PREPARING AN A2A-ADENOSINE RECEPTOR AGONIST AND ITS POLYMORPHS

(75) Inventors: Jeff Zablocki, Mountain View, CA (US); Elfatih Elzein, Fremont, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/092,812

(22) Filed: Apr. 22, 2011

(65) Prior Publication Data

US 2011/0257387 A1    Oct. 20, 2011

Related U.S. Application Data

(63) Continuation of application No. 12/687,077, filed on Jan. 13, 2010, now Pat. No. 7,956,179, which is a continuation of application No. 11/750,295, filed on May 17, 2007, now Pat. No. 7,671,192, which is a continuation-in-part of application No. 11/701,699, filed on Feb. 2, 2007, now Pat. No. 7,732,595.

(60) Provisional application No. 60/765,114, filed on Feb. 3, 2006, provisional application No. 60/801,857, filed on May 18, 2006.

(51) Int. Cl.
C07H 19/00       (2006.01)
C07H 19/167      (2006.01)
C07H 19/173      (2006.01)

(52) U.S. Cl. ............... 536/27.11; 536/27.63; 536/27.7
(58) Field of Classification Search .................. None
See application file for complete search history.

(56) References Cited

U.S. PATENT DOCUMENTS

| | | | |
|---|---|---|---|
| 3,845,770 A | 11/1974 | Theeuwes et al. |
| 4,089,959 A | 5/1978 | Diamond |
| 4,120,947 A | 10/1978 | Diamond |
| 4,325,956 A | 4/1982 | Kjellin et al. |
| 4,326,525 A | 4/1982 | Swanson et al. |
| 4,593,095 A | 6/1986 | Snyder et al. |
| 4,696,932 A | 9/1987 | Jacobson et al. |
| 4,804,664 A | 2/1989 | Kjellin et al. |
| 4,902,514 A | 2/1990 | Barclay et al. |
| 4,956,345 A | 9/1990 | Miyasaka et al. |
| 4,968,687 A | 11/1990 | Findeisen et al. |
| 4,968,697 A | 11/1990 | Hutchison |
| 4,992,445 A | 2/1991 | Lawter et al. |
| 5,001,139 A | 3/1991 | Lawter et al. |
| 5,032,252 A | 7/1991 | Owen et al. |
| 5,070,877 A | 12/1991 | Mohiuddin et al. |
| 5,189,027 A | 2/1993 | Miyashita et al. |
| 5,270,304 A | 12/1993 | Kogi et al. |
| 5,459,254 A | 10/1995 | Yamaguchi et al. |
| 5,516,894 A | 5/1996 | Reppert |
| 5,593,975 A | 1/1997 | Cristalli |
| 5,616,345 A | 4/1997 | Geoghegan et al. |
| 5,641,784 A | 6/1997 | Kufner-Muhl et al. |
| 5,646,156 A | 7/1997 | Jacobson et al. |
| 5,670,498 A | 9/1997 | Suzuki et al. |
| 5,703,085 A | 12/1997 | Suzuki et al. |
| 5,704,491 A | 1/1998 | Graves |
| 5,705,491 A | 1/1998 | Yamada |
| 5,770,716 A | 6/1998 | Khan et al. |
| 5,776,960 A | 7/1998 | Oppong et al. |
| 5,780,481 A | 7/1998 | Jacobson et al. |
| 5,854,081 A | 12/1998 | Linden et al. |
| 5,877,180 A | 3/1999 | Linden et al. |
| 5,939,543 A | 8/1999 | Morozumi et al. |
| 6,026,317 A | 2/2000 | Verani |
| 6,117,878 A | 9/2000 | Linden |
| 6,214,807 B1 | 4/2001 | Zablocki et al. |
| 6,294,522 B1 | 9/2001 | Zablocki et al. |
| 6,322,771 B1 | 11/2001 | Linden et al. |
| 6,368,573 B1 | 4/2002 | Leung |
| 6,387,913 B1 | 5/2002 | Mustafa |
| 6,403,567 B1 | 6/2002 | Elzein et al. |
| 6,448,235 B1 | 9/2002 | Linden et al. |
| 6,514,949 B1 | 2/2003 | Linden et al. |
| 6,552,023 B2 | 4/2003 | Zablocki et al. |
| 6,599,283 B1 | 7/2003 | Marzilli et al. |
| 6,605,597 B1 | 8/2003 | Zablocki et al. |
| 6,642,210 B1 | 11/2003 | Zablocki et al. |
| 6,670,334 B2 | 12/2003 | Linden et al. |
| 6,677,336 B2 | 1/2004 | Zablocki et al. |
| 6,758,388 B1 | 7/2004 | Leholm et al. |
| 6,770,634 B1 | 8/2004 | Zablocki et al. |

(Continued)

FOREIGN PATENT DOCUMENTS

CA             965411          4/1975

(Continued)

OTHER PUBLICATIONS (R) Brady et al., "General Chemistry—Principles and Structure," John Wiley & Sons, New York, NY, 1978, only pp. 328-330 and 352-353 supplied.*
Korolkovas, Essentials of Molecular Pharmacology-Background for Drug Design, Wiley—Interscience, New York, NY, 1970, only pp. 266-272 supplied.
Office Action for U.S. Appl. No. 11/864,437, dated Mar. 29, 2011, 12 pages.
Office Action for U.S. Appl. No. 11/969,047, dated Mar. 17, 2011, 13 pages.
Office Action for U.S. Appl. No. 12/435,176, dated Apr. 15, 2011, 12 pages.
Office Action for U.S. Appl. No. 12/637,583, dated Apr. 4, 2011, 10 pages.
Office Action for U.S. Appl. No. 12/695,096, dated Apr. 14, 2011, 8 pages.
Office Action for U.S. Appl. No. 12/765,623, dated Mar. 8, 2011, 7 pages.
Office Action for U.S. Appl. No. 11/766,964, dated Apr. 7, 2011, 16 pages.

(Continued)

Primary Examiner — Lawrence E Crane
(74) Attorney, Agent, or Firm — Foley & Lardner LLP

(57) ABSTRACT

Disclosed is a synthesis suitable for large scale manufacture of an $A_{2A}$-adenosine receptor agonist, and also relates to polymorphs of that compound, and to methods of isolating a specific polymorph.

16 Claims, 5 Drawing Sheets

U.S. PATENT DOCUMENTS

| | | | |
|---|---|---|---|
| 6,825,349 B2 | 11/2004 | Kalla et al. | |
| 6,855,818 B2 | 2/2005 | Zablocki et al. | |
| 6,916,804 B2 | 7/2005 | Castelhano et al. | |
| 6,977,300 B2 | 12/2005 | Kalla et al. | |
| 6,995,148 B2 | 2/2006 | Jones et al. | |
| 7,109,180 B2 | 9/2006 | Zablocki et al. | |
| 7,109,203 B2 | 9/2006 | Hart et al. | |
| 7,125,993 B2 | 10/2006 | Elzein et al. | |
| 7,144,872 B2 | 12/2006 | Zablocki et al. | |
| 7,183,264 B2 | 2/2007 | Zablocki et al. | |
| 7,553,823 B2 | 6/2009 | Zablocki et al. | |
| 7,582,617 B2 | 9/2009 | Belardinelli et al. | |
| 7,655,636 B2 | 2/2010 | Gordi et al. | |
| 7,655,637 B2 | 2/2010 | Zablocki et al. | |
| 7,671,192 B2 * | 3/2010 | Zablocki et al. | 536/27.11 |
| 7,683,037 B2 | 3/2010 | Belardinelli | |
| 7,732,595 B2 * | 6/2010 | Zablocki et al. | 536/27.11 |
| 7,956,179 B2 * | 6/2011 | Zablocki et al. | 536/27.11 |
| 2002/0012946 A1 | 1/2002 | Belardinelli et al. | |
| 2002/0111327 A1 | 8/2002 | Linden et al. | |
| 2002/0147174 A1 | 10/2002 | Jones et al. | |
| 2003/0235555 A1 | 12/2003 | Shealey et al. | |
| 2004/0038928 A1 | 2/2004 | Zablocki et al. | |
| 2004/0064039 A1 | 4/2004 | Belardinelli | |
| 2004/0137533 A1 | 7/2004 | Belardinelli et al. | |
| 2005/0020915 A1 | 1/2005 | Belardinelli et al. | |
| 2005/0175535 A1 | 8/2005 | Belardinelli et al. | |
| 2006/0084625 A1 | 4/2006 | Gordi et al. | |
| 2006/0159621 A1 | 7/2006 | Barrett | |
| 2006/0159627 A1 | 7/2006 | Zeng et al. | |
| 2007/0114269 A1 | 5/2007 | Straza | |
| 2007/0203090 A1 | 8/2007 | Zablocki et al. | |
| 2007/0207978 A1 | 9/2007 | Zablocki et al. | |
| 2007/0265445 A1 | 11/2007 | Zablocki et al. | |
| 2007/0299089 A1 | 12/2007 | Belardinelli et al. | |
| 2008/0170990 A1 | 7/2008 | Lieu et al. | |
| 2008/0213165 A1 | 9/2008 | Lieu et al. | |
| 2008/0267861 A1 | 10/2008 | Lieu et al. | |
| 2009/0081120 A1 | 3/2009 | Lieu et al. | |
| 2009/0317331 A1 | 12/2009 | Belardinelli et al. | |
| 2010/0081810 A1 | 4/2010 | Zablocki et al. | |
| 2010/0086483 A1 | 4/2010 | Belardinelli et al. | |
| 2010/0158797 A1 | 6/2010 | Gordi et al. | |
| 2010/0160620 A1 | 6/2010 | Zablocki et al. | |
| 2010/0179313 A1 | 7/2010 | Zablocki et al. | |
| 2010/0183503 A1 | 7/2010 | Belardinelli | |
| 2010/0272645 A1 | 10/2010 | Belardinelli | |

FOREIGN PATENT DOCUMENTS

| | | |
|---|---|---|
| CA | 2064742 | 12/1991 |
| CA | 2377746 | 12/2000 |
| EP | 0 354 638 | 2/1990 |
| EP | 0 386 683 | 9/1990 |
| JP | SHO 48-26038 | 8/1973 |
| JP | Hei 5 1993 9197 | 1/1993 |
| WO | WO 92/00297 | 1/1992 |
| WO | WO 92/12260 | 7/1992 |
| WO | WO 93/23401 | 11/1993 |
| WO | WO 93/25677 | 12/1993 |
| WO | WO 95/11681 | 5/1995 |
| WO | WO 98/52611 | 11/1998 |
| WO | WO 98/57651 | 12/1998 |
| WO | WO 99/63938 | 12/1999 |
| WO | WO 00/78778 | 12/2000 |
| WO | WO 00/78779 | 12/2000 |
| WO | WO 01/16134 | 8/2001 |
| WO | WO 01/62979 | 8/2001 |
| WO | WO 03/088978 | 10/2003 |
| WO | WO 2004/011010 | 2/2004 |
| WO | WO 2005/082379 | 9/2005 |
| WO | WO 2006/076698 | 7/2006 |
| WO | WO 2007/092372 | 8/2007 |
| WO | WO 2008/028140 | 3/2008 |
| WO | WO 2008/042796 | 4/2008 |
| WO | WO 2008/063712 | 5/2008 |
| WO | WO 2008/086096 | 7/2008 |
| WO | WO 2008/143667 | 11/2008 |
| WO | WO 2006/044856 | 4/2009 |
| WO | WO 2009/076580 | 6/2009 |
| WO | WO 2010/037122 | 4/2010 |

OTHER PUBLICATIONS

Sambuceti et al., Coronary Vasoconstriction During Myocardial Ischemia Induced by Rises in Metabolic Demand in Patients with Coronary Artery Disease, Circulation, 1997; 95; (2652-2659) pp. 1-24.

Sambuceti et al., Interaction Between Coronary Artery Stenosis and Coronary Microcirculation in Ischemic Heart Disease, Z Kardiol, 2000; 89 Suppl 9:IX/126-31, abstract.

Bergmann et al., "Oxidation of Hypoxanthines, Bearing 8-Aryl or 8-Pyridyl Substituents, by Bovine Milk Xanthine Oxidase,", Biochimica et Biophysica Acta, vol. 484, No. 2, pp. 275-289 (1977).

Birdsall et al., "Purine N-Oxides-XL the 3-Acyloxypurine 8-Substitution Reaction: Scope: Syntheses of 8-Substituted Xanthines and Guanines," Tetrahedron, vol. 27, pp. 5969-5978 (1971).

Blackburn et al., "Adenosine Mediates IL-13-Induced Inflammation and Remodeling in the Lung and interacts in an IL 13-Adenosine Amplification Pathway," J. Clin. Invest. vol. 112, No. 3, pp. 332-344 (2003).

Bruns, "Adenosine Antagonism by Purines, Pteridines and Benzopteridines in Human Fibroblasts," Biochemical Pharmacology, vol. 30, No. 4, pp. 325-333 (1981).

Buckle et al., "Inhibition of Cyclic Nucleotide Phosphodiesterase by Derivatives of 1,3-Bis(cyclopropylmethyl)xanthine," J. Med. Chem., vol. 37, pp. 476-485 (1994).

Cerqueira, "The Future of Pharmacologic Stress: Selective A2A Adenosine Receptor Agonists," Am. J. Cardiol., vol. 94 (2A), pp. 33D-42D (2004).

Cline et al., "Coronary Artery Angiography Using Multislice Computed Tomography Images," Circulation, vol. 102, pp. 1589-1590, XP002564059 (2000).

Crimi et al., "Purine Derivatives in the Study of Allergic Inflammation in Respiratory Diseases," Allergy, vol. 52, No. 34, pp. 48-54 (1997).

Cristalli et al., "2-Alkynyl Derivatives of Adenosine 5'-N'ethyluronamide: Selective A2 Adenosine Receptor Agonists with Potent Inhibitory Activity on Platelet Aggretation," J. Med. Chem., vol. 37, pp. 1720-1726 (1994).

Cushley et al., "Inhaled Adenosine and Guanosine on Airway Resistance in Normal and Asthmatic Subjects," Br. J. Clin. Pharmacol, vol. 15, No. 2, pp. 161-165 (1983).

Dalpiaz et al., "De Novo Analysis of Receptor Binding Affinity Data of Xanthine Adenosine Receptor Antagonists," Arzneim-Forsch/Drug Res., vol. 45, No. 3, pp. 230-233 (1995).

Dhalla et al., "Tachycardia Caused by A2A Adenosine Receptor Agonists is Mediated by Direct Sympathoexcitation in Awake Rates," Journal of Pharmacology and Experimental Therapeutics, USA, vol. 316, No. 2, pp. 695-702, XP009073100 (2006).

Driver et al., "Adenosine in Bronchoalveolar Lavage Fluid in Asthma," Am. Rev. Respir. Dis., vol. 148, No. 1, pp. 91-97 (1993).

Elias et al., "Airway Remodeling in Asthma," The Journal of Clinical Investigation, vol. 104, No. 8, pp. 1001-1006 (1999).

Erickson et al., "1,3,8-Trisubstituted Xanthines. Effects of Substitution Pattern upon Adenosine Receptor $A_1/A_2$ Affinity", J. Med. Chem., vol. 34, pp. 1431-1435 (1991).

Feoktistov et al., "Adenosine $A_{2B}$ Receptors: A Novel Therapeutic Target in Asthma," Trends Pharmacol. Sci., vol. 19, pp. 148-153 (1998).

Feoktistov et al., "Hypoxia Modulates Adenosine Receptors in Human Endothelial and Smooth Muscle Cells Toward an A2B Angiogenic Phenotype," Hypertension, vol. 44, No. 5, pp. 649-654, Epub 2004, PMID: 15452028 [PubMed—indexed for MEDLINE] (2004).

Gao et al., "Novel Short-Acting A2A Adenosine Receptor Agonists for Coronary Vasodilation: Inverse Relationship between Affinity and Duration of Action of A2A Agonists," Journal of Pharmacology and Experimental Therapeutics, vol. 298, pp. 209-218 (2001).

Glover et al., "Characterization of a New, Highly Selective Adenosine A2A Receptor Agonist with Potential Use in Pharmacologic Stress Perfusion Imaging", Circulation, vol. 110, pp. I-311 (1999).

Glover et al., "Pharmacological Stress Thallium Scintigraphy with 2-cyclohexylmethylidenehydrazinoadenosine (WRC-0470)," Circulation, vol. 94, pp. 1726-1732 (1996).

Harvey, "Blood Fluids, Electrolytes and Hematologic Drugs," Chapter 40 in Remington's Pharmaceutical Sciences, 18$^{th}$ Ed., Gennaro et al., Mack Publishing Co., East, PA, only pp. 800 and 821 supplied (1990).

Hendel et al. "Initial Clinical Experience with Regadenoson, a Novel Selective A2A Agonist for Pharmacologic Stress Single-Photon Emission Computed Tomography Myocardial Perfusion Imaging", Journal of the American College of Cardiology, vol. 46, No. 11, pp. 2069-2075 (2005).

Hendel et al., "Pharmacologic Stress SPECT Myocardial Perfusion Imaging with a Selective A2A Agonist: Results of a Pilot Study Comparing Adenosine with CVT-3146", Circulation, Supplement IV, vol. 108, pp. 2892 (2003).

Holgate et al., "Roles of Cysteinyl Leukotrienes in Airway Inflammation, Smooth Muscle Function and Remodeling," J. Allergy Clin. Imunol. (Suppl):S18-34; discussion S34-6, Review, PMID:12532084 [PubMed- indexed for MEDLINE](2003).

Hoshino, "Impact of Inhaled Corticosteriods and Leukotrience Receptor Antagonists on Airway Remodeling," Clinical Reviews in Allergy & Immunology, vol. 27, No. 1, pp. 59-64 (2004).

Iskandrian, "Adenosine Myocardial Perfusion Imaging," The Journal of Nuclear Medicine, vol. 35, pp. 734-736 (1994).

Jacobson et al., "1,3-Dialkylxanthine Derivatives Having High Potency as Antagonists at Human $A_{2B}$ Adenosine Receptors," Drug Development Research, vol. 47, pp. 45-53 (1999).

Jadbabaie et al., "Myocardial perfusion imaging with a novel selective A2A Adenosine Receptor Agonists (CVT-3146): Important differences in radiotracer behavior," Journal of Am. Col. Cardiology, vol. 41, pp. 443-444 (2003).

Jeffery, "Remodeling in Asthma and Chronic Obstructive Lung Disease," Am. J. Respir. Crit. Care Med., vol. 164, No. 10pt2, pp. S28-S38 (2001).

Katsushima et al., "Structure-Activity Relationships of 8-Cycloalkyl-1,3-dipropylxanthines as Antagonist of Adenosine Receptors," J. Med. Chem., vol. 33, pp. 1906-1910 (1990).

Kerensky et al. "Dose Dependent Increase in Human Coronary Blood Flow Velocity Following an IV Bolus of CVT-3146, A Novel A2A Adenosine Receptor Agonists: A Potential Agent for the Use in Pharmacological Stress Testing for Myocardial Perfusion Imaging" Circulation, Supplemental II, vol. 106, vol. 19, pp. II-618, (2002).

Kim et al., "Acyl-Hydrazide Derivatives of a Xanthine Carboxylic Congener (XCC) as Selective Antagonists at Human $A_{2B}$ Adenosine Receptors", Drug Development Research, vol. 47, pp. 178-188 (1999).

Kleiner, "Reactions of Some 8-(3-Pyridyl)-6-thioxanthines with Methyl Iodide," pp. 739-743 (1973).

Klotz et al., "Comparative pharmacology of human adenosine receptors subtypes-characterization of stably transfected receptors in CHO cells," Nauny-Schmideberg's Arch Pharmacol., vol. 357, pp. 1-9 (1998).

Koepfli et al., "Interaction of caffeine with regadenoson-induced hyperemic myocardial blood flow as measured by PET", European Heart Journal, vol. 27, No. Supp. 1, p. 175, (2006).

Korolkovas, Essentials of Molecular Pharmacology-Background for Drug Design, Wiley—Interscience, New York, NY, only pp. 266-272 supplied, (1970).

Kubo et al., "Effect of Caffeine Intake on Myocardial Hyperemic Flow Induced by Adenosine Triphosphate and Dipyridamole," The Journal of Nuclear Medicine, vol. 45, No. 5, pp. 730-738, (2004).

Leigh et al., "Is Interleukin-1 3 Critical in Maintaining Airway Hyperresponsiveness in Allergen-Challenged Mice?" Am. J. Respir. Crit. Care Med., PMID: 15242841 [PubMed—indexed for MEDLINE] vol. 170, No. 8, pp. 851-856 (2004).

Kusmic et al., "Coronary microcirculatory vasoconstriction induced by low-flow ischemia in mouse hearts is reversed by an A2A adenosine receptor", FASEB Journal, pp. A1227-A1228 (2007).

Linden et al., "Characterization of Human $A_{2B}$ Adenosine Receptors: Radioligand Binding, Western Blotting and Coupling to Gq in Human Embryonic Kidney 293 Cells and HMC-1 Mast Cells," Molecular Pharmacology, vol. 56, pp. 705-713 (1999).

Mager et al., "Molecular Simulation Applied to 2-(N'-alkylidenehydrazino)-and 2-(N'-aralkylidenehydrazino) adenosine A2 Agonists," European Journal of Medicinal Chemistry, vol. 30, pp. 15-25 (1995).

Mann et al., "Airway Effects of Purine Nucleosides and Nucleotides and Release With Bronchial Provocation in Asthma," J. Appl. Physiol., vol. 61, No. 5, pp. 1667-1676 (1986).

Martin et al., "Pharmacology of 2-cylohexylmethylidenehydrazionoadenosine (WRC-0470), a novel, short-acting adenosine A-2A receptor agonist that produces selective coronary vasodilation", Drug Development Research, vol. 40, No. 4, pp. 313-324, (1997).

Martinson et al., "Potent Adenosine Receptor Antagonists that are Selective for the $A_1$ Receptor Subtype," Molecular Pharmacology, vol. 31, No. 3, pp. 247-252 (1986).

Marumoto et al. (I), "Synthesis and Coronary Vasodilating Activity of 2-Substituted Adenosines," Chemical Pharmaceutical Bulletin, vol. 23, No. 4, pp. 759-774 (1975).

Marumoto et al. (II), "Synthesis and Enzymatic Activity of Adenosine 3',5'-Cyclic Phosphate Analogues," Chemical Pharmaceutical Bulletin, vol. 27, No. 4, pp. 990-1003 (1979).

Matsuda et al., "Nucleosides and Nucleotides, 103. 2-Alkynyladenoines: A Novel Class of Selective Adenosine A2 Receptor Agonists with Potent Antihypertensive Effects," Journal of Medicinal Chemistry, vol. 35, No. 1, pp. 241-252 (1992).

Mosselhi et al., "Reactions of some 8-diazoxanthine derivatives", Indian Journal of Chemistry, vol. 33B, pp. 236-242 (1994).

Niiya et al., "2-(N'-Alkylidenehydrazino) Adenosines; Potent and Selective Coronary vasodilators," Journal of Medicinal Chemistry, American Chemical Society, vol. 35, No. 24, pp. 4557-4561, (1992).

Ogden, et al., Mean Body Weight, Height, and Body Mass Index, United States 1960-2002, U.S. National Health and Nutrition Examination Survery, Advance Data No. 347, pp. 1-18, (2004).

Persson et al., "Synthesis and Antiviral Effects of 2-Heteroaryl Substituted Adenosine and 8-Heteroaryl Guanosine Deriviatives," Bioorganic & Medicinal Chemistry, vol. 3, No. 10, pp. 1377-1382 (1995).

Pfizer, "Health info.", (2003), http://www.pfizer.be/English/What_we_do_/Health_info/COPD.htm.

Pifferi et al., "Montelukast and Airway Remodeling in Children with Chronic Persistent Asthma: An Open Study," Pediatric Allergy and Immunology, vol. 15, No. 5, pp. L472-473 (2004).

Polosa et al., "Evolving Concepts on the Value of Adenosine Hyperresponsiveness in Asthma and Chronic Obstructive Pulmonary Disease". Thorax, vol. 57, No. 7, pp. 649-654 (2002).

Polosa, "Adenosine-Receptor Subtypes: The Relevance to Adenosine-Mediated Responses in Asthma and Chronic Obstructive Pulmonary Disease," The European Respiratory Journal: Official Journal of the European Society for Clinical Respiratory Physiology., vol. 20, No. 2, pp. 488-496 (2002).

Riou et al., "Influence of propranolol, enalaprilat, verapamil, and caffeine on adenosine A(2A) receptor medicated coronary vasodilation", Journal of the American College of Cardiology, vol. 40, No. 9, pp. 1687-1690 (2002).

Roth et al., "8-Dicyclopropylmethyl)-1,3-dipropylxanthine: A Potent and Selective Adenosine A1 Antagonist with Renal Protective and Diuretic Activities," J. Med. Chem., vol. 34, No. 1, pp. 466-469 (1991).

Ryzhov et al., "Adenosine-Activated Mast Cells Induce IgE Synthesis by B Lymphocytes: An $A_{2B}$-Mediated Process Involving the Cytokines IL-4 and IL-13 with Implications for Asthma," vol. 172, No. 12, pp. 7726-7733, PMID: 15187156 [PubMed—indexed for MEDLINE] (2004).

Shimada et al., "8-Polycycloalkyl-l,3-dipropylxanthines as Potent and Selective Antagonists for A1—Adenosine Receptors," J. Med. Chem., vol. 35, pp. 924-930 (1992).

Spicuzza et al., "The Role of Adenosine as a Novel Bronchoprovocant in Asthma," Curr. Opin. Allergy Clin. Immunol., vol. 3, No. 1, pp. 65-69 (2003).

Spicuzza et al., "Research Applications and Implications of Adenosine in Diseased Airways," Trends Pharmacol. Sci., vol. 24, No. 8, pp. 409-413, Review, PMID: 12915050 [Pubmed—indexed for MEDLINE] (2003).

Swinyard et al., "Pharmaceutical Necessities," Chapter 66 in Remington's Pharmaceutical Sciences, 18th Ed., Gennaro et al. (eds.), Mack Publishing Co, Easton, PA, only pp. 1318-1319 supplied (1990).

Swinyard et al., "Pharmaceutical Necessities," Chapter 66 in Remington's Pharmaceutical Sciences, 18th Ed., Gennaro et al. (eds.), Mack Publishing Co, Easton, PA, only pp. 1286-1329 supplied (1990).

Tomita et al., Artificial Neural Network Approach for Selection of Susceptible single Nucleotide Polymorphisms and Construction of Prediction Model on Childhood allergic Asthma: BMC Bioinformatics, vol. 1, No. 5, p. 120, PMID: 15339344 [PubMed—indexed for MEDLINE] (2004).

Trochu et al., "Selective A2A Adenosine Receptor Agonist as a Coronary Vasodilator in Conscious Dogs: Potential for Use in Myocardial Perfusion Imaging," Journal of Cardiovascular, vol. 41, No. 1, pp. 132-139 (2003).

Udelson et al., "Randomized, Controlled Dose-Ranging Study of the Selective Adenosine $A_{2A}$ Receptor Agonist Binodenoson for Pharmacological Stress as an Adjunct to Myocardial Perfusion Imaging," Circulation, vol. 209, pp. 457-464 (2004).

Van Der Wenden et al., "Mapping the Xanthine C8-region of the adenosine $A_1$ Receptor with Computer Graphics," European Journal of Pharmacology-Molecular Pharmacology Section, vol. 206, No. 1, pp. 315-323 (1991).

Xu et al., "Coronary Vasodilation by a Short Acting, Low Affinity A2A Adenosine Receptor Agonist in Anesthetize Closed Chest Dogs: A Second Generation of Coronary Artery Pharmacologic Stressor", Circulation, vol. 102, No. 18, p. 3912 (2000).

Zablocki et al., "2 Substituted PI System Derivatives of Adenosine That Are Coronary Vasodilators Acting Via the A2A Adenosine Receptor", (2001) Nucleosides, Nucleotides and Nucleic Acids 20: (4-7), pp. 343-360.

Zhao et al., "Caffeine attenuates the duration of coronary vasodilation and changes in hemodynamics induced by regadenoson (CVT-3146), a novel adenosine A2A receptor agonist," Journal of Cardiovascular Pharmacology, Raven Press, New York, NY, vol. 49, No. 6, pp. 369-375, XP009094871 (2007).

Zhao et al., "Comparative Profile of Vasodilation by CVT-3146, a novel $A_{2A}$ receptor agonist and adenosine in conscious dogs," Journal of Pharm & Experimental Therapeutics, Journal of Pharm. & Experimental Therapeutics, vol. 41, pp. 182-189 (2003).

Zhao et al., "Effects of caffeine on coronary vasodilation and sinue tachycardia induced by Regadenoson, a novel adenosine A2A receptor agonist, in conscious dogs," European Heart Journal, vol. 27, No. Suppl. 1, p. 424 (2006).

Zhao et al., "Regadenoson, a novel pharmacologic stress agent for use in myocardial perfusion imaging, does not have a direct effect on the QT interval in conscious dogs," Journal of Cardio Vascular Pharmacology, pp. 467-473, vol. 52, No. 5, Lippincott Williams and Wilkins, USA, XP8117431 (2008).

Zhong et al., "Synergy Between A2B Adenosine Receptors and Hypoxia in Activating Human Lung Fibroblasts," American Journal of Respiratory Cell and Molecular Biology, vol. 32, No. 1, pp. 2-8 (2005).

Office Action for U.S. Appl. No. 12/569,643, dated Aug. 25, 2011, 25 pages.

Office Action for U.S. Appl. No. 12/968,110, dated Aug. 3, 2011, 53 pages.

Office Action for U.S. Appl. No. 12/695,096, dated Oct. 5, 2011, 11 pages.

Riou et al. "Influence of Propranolol, Enalaprilat, Verapamil, and Caffeine on Adenosine A2A-Receptor-Mediated Coronary Vasodilation," Journal of the American College of Cardiology, vol. 40, No. 9, pp. 1687-1694, 2002.

\* cited by examiner

PROCESS FOR PREPARING AN A2A-ADENOSINE RECEPTOR AGONIST AND ITS POLYMORPHS

This application is a continuation of U.S. patent application Ser. No. 12/687,077, filed Jan. 13, 2010, now U.S. Pat. No. 7,956,179, which claims priority to U.S. patent application Ser. No. 11/750,295, filed May 17, 2007, now U.S. Pat. No. 7,671,192, which is a continuation-in-part of U.S. patent application Ser. No. 11/701,699, filed Feb. 2, 2007, now U.S. Pat. No. 7,732,595, which claims priority to U.S. Provisional Patent Application Ser. No. 60/801,857, filed May 18, 2006, and to U.S. Provisional Patent Application Ser. No. 60/765,114, filed Feb. 3, 2006, which are hereby incorporated by reference in their entirety.

FIELD OF THE INVENTION

The present invention relates to a process for the large scale preparation of an $A_{2A}$-adenosine receptor agonist, and also relates to polymorphs of that compound, and to methods of isolating a specific polymorph.

BACKGROUND

Adenosine is a naturally occurring nucleoside, which exerts its biological effects by interacting with a family of adenosine receptors known as $A_1$, $A_{2A}$, $A_{2B}$, and $A_3$, all of which modulate important physiological processes. One of the biological effects of adenosine is to act as a coronary vasodilator; this result being produced by interaction with the $A_{2A}$ adenosine receptor. This effect of adenosine has been found to be useful as an aid to imaging of the heart, where coronary arteries are dilated prior to administration of an imaging agent (for example, thallium 201), and thus, by observation of the images thus produced, the presence or absence of coronary artery disease can be determined. The advantage of such a technique is that it avoids the more traditional method of inducing coronary vasodilation by exercise on a treadmill, which is clearly undesirable for a patient that has a coronary disease.

However, administration of adenosine has several disadvantages. Adenosine has a very short half life in humans (less than 10 seconds), and also has all of the effects associated with $A_1$, $A_{2A}$, $A_{2B}$, and $A_3$ receptor agonism. Thus the use of a selective $A_{2A}$ adenosine receptor agonist would provide a superior method of producing coronary vasodilation, particularly one with a longer half life and few or no side effects.

A class of compounds possessing these desirable properties was disclosed in U.S. Pat. No. 6,403,567, the complete disclosure of which is hereby incorporated by reference. In particular, one compound disclosed in this patent, (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide, has been shown to be a highly selective $A_{2A}$-adenosine receptor agonist, and is presently undergoing clinical trials as a coronary vasodilator useful in cardiac imaging.

Given the heightened interest in this and similar compounds, it has become desirable to find new methods of synthesis that provide a convenient method for making large quantities of the material in good yield and high purity. The patent that discloses the compound of interest (U.S. Pat. No. 6,403,567) provides several methods for preparing the compound. However, although these methods are suited to small scale syntheses, all synthetic methods disclosed in the patent utilize protecting groups, which is undesirable for large scale syntheses.

Additionally, it was discovered that the desired product (that is (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide) is capable of existing in at least three different crystalline forms, the most stable of which is a monohydrate. This polymorph is stable under relative humidity stress conditions, up to its melting point. Accordingly, it is desirable that the final product produced in the new syntheses is obtained as the stable monohydrate.

SUMMARY OF THE INVENTION

Thus, it is an object of this invention to provide convenient syntheses for the large scale preparation of (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide, and polymorphs thereof, preferably as its monohydrate. Accordingly, in a first aspect, the invention relates to the preparation of a compound of the Formula I:

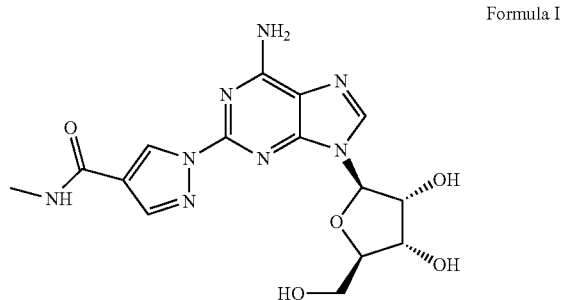

Formula I comprising:

contacting a compound of the formula (3):

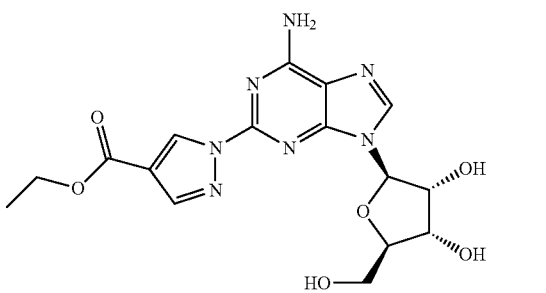

(3)

with methylamine.

In one embodiment the reaction is conducted in an aqueous solution of methylamine, initially at a temperature of about 0-5° C., followed by warming to about 50-70° C. Alternatively, the reaction is conducted as above but in a sealed pressure reactor.

In a second embodiment, the product is isolated as the pure monohydrate by dissolving the product in a solvent, for example dimethylsulfoxide, addition of purified water, filtering the slurry thus formed, washing the contents of the filter with water followed by ethanol, and drying the solid that remains under vacuum at a temperature that does not exceed 40° C.

In a second aspect, the invention relates to the preparation of a compound of the formula (3):

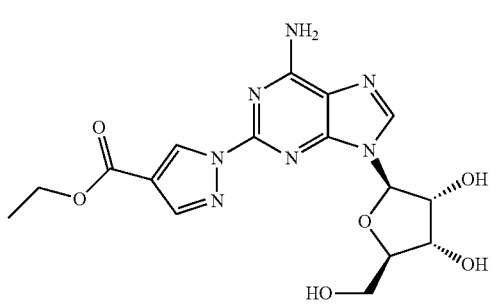
(3)

comprising:
contacting a compound of the formula (2):

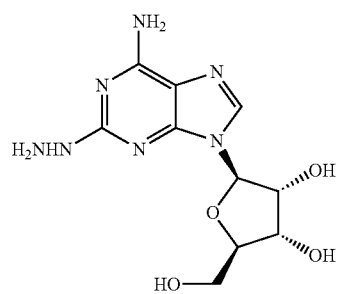
(2)

with ethyl 2-formyl-3-oxopropionate.

In one embodiment, the reaction is conducted in ethanol, at a temperature of about 80° C., with about 1.1 molar equivalents of ethyl 2-formyl-3-oxopropionate.

In a third aspect, the invention relates to the preparation of a compound of the formula (2):

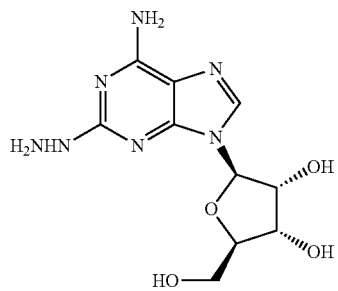
(2)

comprising:
contacting a compound of the formula (1):

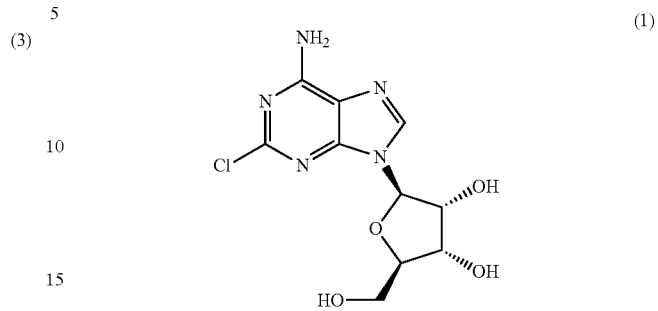
(1)

with hydrazine.

A 14.3-16.7 fold molar excess of hydrazine may be used and the reaction may be conducted at a temperature of approximately 60-65° C. In one embodiment the hydrazine is first heated to approximately 60-65° C. followed by addition of the compound of formula (1). The compound of formula (2) may be isolated by (a) cooling the reaction mixture to approximately 40° C., (b) adding a 4.2-4.9 mass equivalent of water while maintaining the temperature at approximately 40° C., (c) cooling the mixture to approximately 10° C. and maintaining at that temperature for at least approximately 1 hour, (d) filtering, (e) washing the contents of the filter with water followed by ethanol, and (f) drying the solid that remains under vacuum at a temperature that does not exceed 30° C. for at least 12 hours.

The above described synthesis is suitable for the large scale synthesis of the desired product, which is provided in good yield, although one minor impurity is seen in the final product. This impurity has been shown to be unchanged intermediate of the formula (2); that is, the compound of the formula:

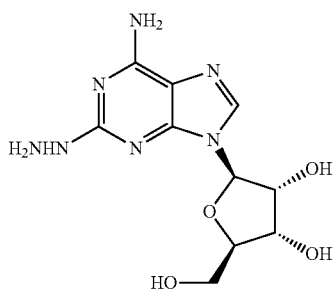
(2)

Although this impurity can be removed from the final product by crystallization, it was decided to seek an alternative synthesis that had all of the advantages of the above synthesis but did not give the compound of formula (2) as an impurity in the final product.

Thus, in a fourth aspect, the invention relates to a method of synthesizing (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide by contacting a compound of the formula (4):

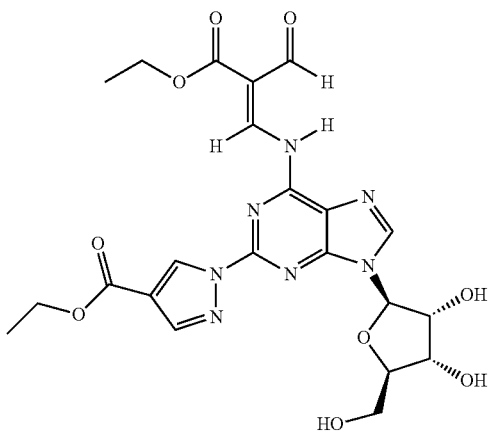

(4)

with methylamine.

In one embodiment the reaction is conducted in an aqueous solution of methylamine, initially at a temperature of about 0-5° C., followed by warming to about 50-70° C. Preferably, the reaction is conducted in a sealed pressure reactor.

In another embodiment, the reaction is conducted at a temperature of approximately 2.5-7.5° C.

In still another embodiment, the product is isolated as the pure monohydrate by dissolving the product in a solvent, for example dimethylsulfoxide, addition of purified water, filtering the slurry thus formed, washing the contents of the filter with water followed by ethanol, and drying the solid that remains under vacuum at a temperature that does not exceed 40° C. In some other embodiments, the product may be isolated as the pure monohydrate by (a) degassing the reaction mixture under vacuum at not more than 35° C. to remove excess methylamine, (b) releasing the vacuum and cooling to 0-5° C. for approximately 15-minutes to an hour, (c) filtering the slurry thus formed, (d) washing the contents of the filter with water followed by ethanol, and (e) drying the solid that remains under vacuum at a temperature that does not exceed 40° C.

In some embodiments the (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide is further purified to provide the monohydrate form by (i) dissolving the compound in a solvent, such as dimethylsulfoxide, heated to approximately 78-88°, (ii) filtering any solid impurities from the solution, (iii) rinsing with additional solvent, (iv) adding solution to purified water that is maintained at approximately 78-88° thereby forming a slurry, (v) stirring the slurry, (vi) cooling the slurry, (vii) filtering, (viii) washing the contents of the filter with water followed by ethanol, and (ix) drying the solid that remains under vacuum at a temperature that does not exceed 40° C.

In a fifth aspect, the invention relates to a method of synthesizing a compound of the formula (4):

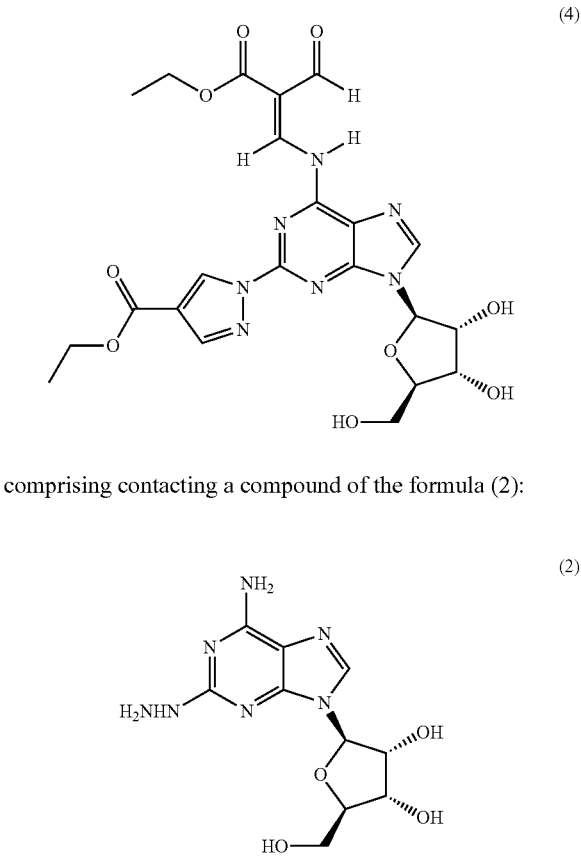

(4)

comprising contacting a compound of the formula (2):

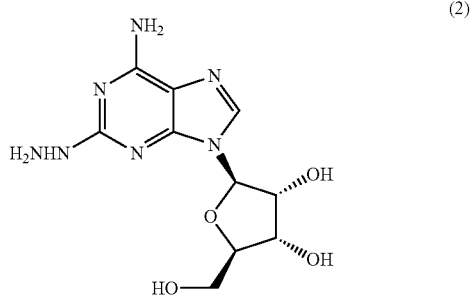

(2)

with an excess of ethyl 2-formyl-3-oxopropionate, preferably about a 2-10 fold molar excess, more preferably about a 5-10 fold excess. In one embodiment, the reaction is conducted in ethanol, at a temperature of about 80° C. The ethyl 2-formyl-3-oxopropionate is present in a 5-10 fold excess.

In a further embodiment, an additional method of synthesizing a compound of the formula (4) is also presented comprising contacting a compound of the formula (2)

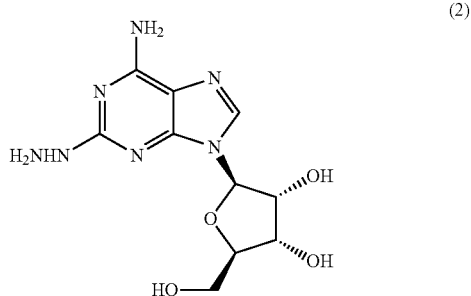

(2)

with an excess of ethyl 2-formyl-3-oxopropionate in the presence of acid. The reaction takes place at reflux is generally conducted in ethanol. The reaction takes place with or without the use of HCl as a catalyst. Up to 0.1 molar equivalent, preferably about a 0.05 molar excess of HCl and about a 5-10 fold molar excess, preferably about a 6.8-7.5 fold molar excess, of ethyl 2-formyl-3-oxoproionate are used. The product of this reaction may be isolated by (a) cooling the completed reaction mixture to approximately 10° C., (b) filtering, (c) washing the contents of the filter with ethanol, and (d) drying the solid that remains under vacuum at a temperature that does not exceed 40° C.

DEFINITIONS AND GENERAL PARAMETERS

As used in the present specification, the following words and phrases are generally intended to have the meanings as set forth below, except to the extent that the context in which they are used indicates otherwise.

"Optional" or "optionally" means that the subsequently described event or circumstance may or may not occur, and that the description includes instances where said event or circumstance occurs and instances in which it does not.

The term "therapeutically effective amount" refers to that amount of a compound of Formula I that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treatment" or "treating" means any treatment of a disease in a mammal, including:

(i) preventing the disease, that is, causing the clinical symptoms of the disease not to develop;
(ii) inhibiting the disease, that is, arresting the development of clinical symptoms; and/or
(iii) relieving the disease, that is, causing the regression of clinical symptoms.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "polymorph" is intended to include amorphous and solvates of (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide.

It has been discovered that this compound is capable of existing in at least three different crystalline forms, referred to herein as Form A, Form B, Form C, and an amorphous product.

Form A: This polymorph can be produced by crystallizing 1-{9-[(4S,2R,3R,5R)-3,4-dihydroxy-5-(hydroxymethyl)oxolan-2-yl]-6-aminopurin-2-yl}pyrazol-4-yl)-N-methylcarboxamide from protic solvents, for example ethanol or ethanol/water mixtures, or from a polar solvent, for example dimethylsulfoxide/water. Form A has been shown to be a monohydrate, and is the most stable of the various polymorphs at ambient temperatures. It is stable under relative humidity stress conditions up to its melting point.

Figure 4:
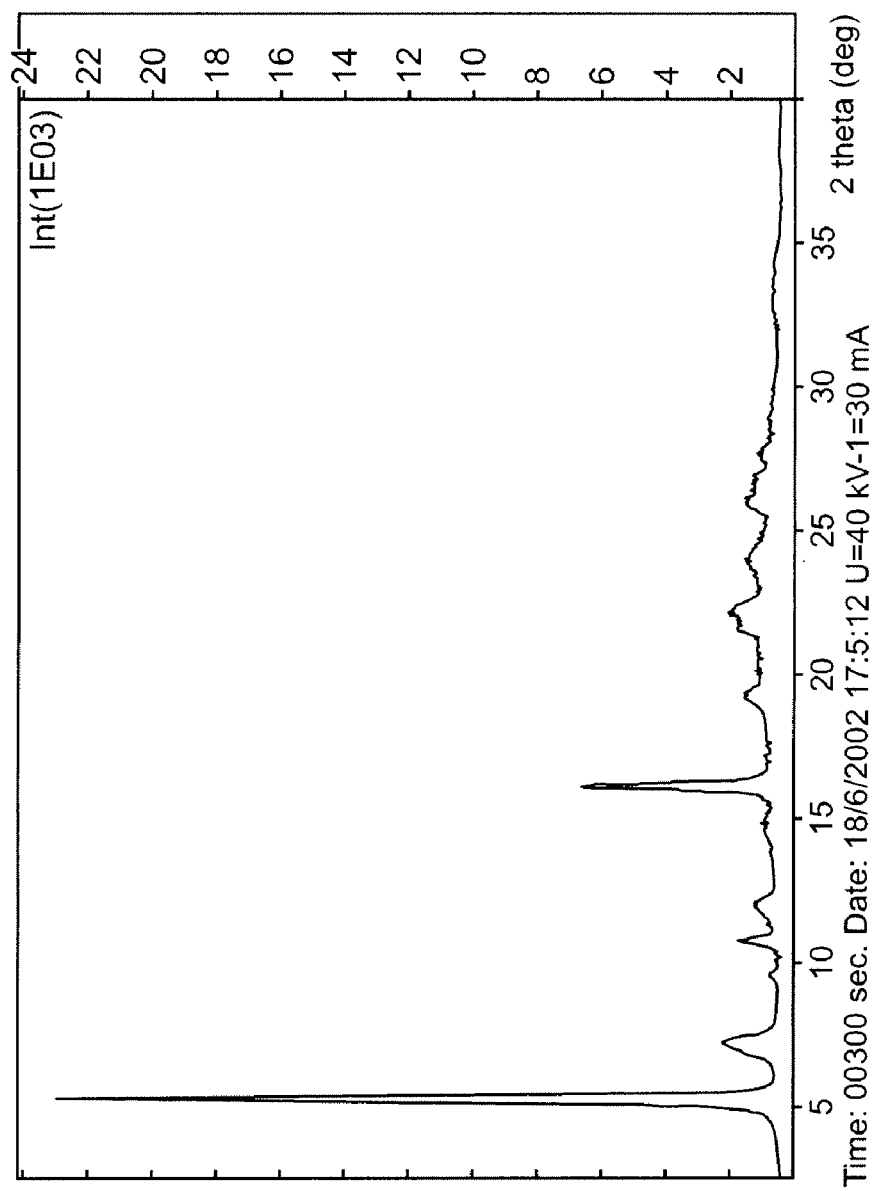
FIG. 4 shows the X-Ray diffraction pattern for (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide Form B.

Form B: This polymorph is produced by evaporating under vacuum a solution of 1-{9-[(4S,2R,3R,5R)-3,4-dihydroxy-5-(hydroxymethyl)oxolan-2-yl]-6-aminopurin-2-yl}pyrazol-4-yl)-N-methylcarboxamide in trifluoroethanol at ambient temperatures. The X-ray analysis of the crystals was distinctly different from any other polymorph (see FIG. 4), but it was difficult to determine its constitution, as the X-ray analysis gave disordered broad peaks, and the polymorph contained varying amounts of water. It was found to be difficult to reliably reproduce the preparation of this polymorph.

Figure 5:
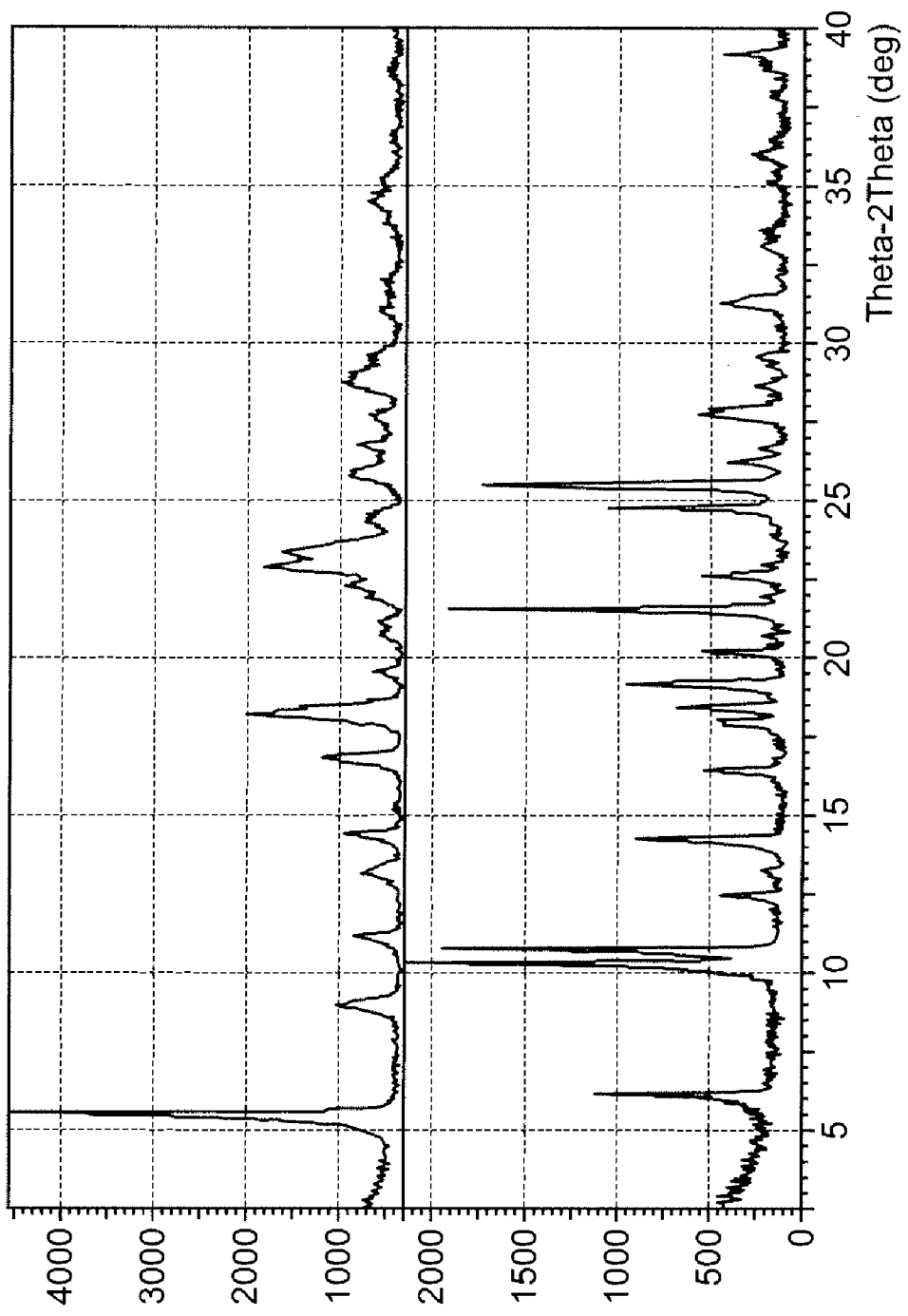
FIG. 5 shows the X-Ray diffraction pattern for (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide Form C as compared to Form A.

Form C: This polymorph is produced by slurrying 1-{9-[(4S,2R,3R,5R)-3,4-dihydroxy-5-(hydroxymethyl)oxolan-2-yl]-6-aminopurin-2-yl}pyrazol-4-yl)-N-methylcarboxamide in acetonitrile for a long period of time at 60° C. The X-ray analysis of the crystals was distinctly different from any other polymorph (see FIG. 5). Polymorph C was shown to be a variable hydrate, which, at elevated temperatures, desolvates to an unstable form.

Amorphous Material: This polymorph is produced by heating Form A polymorph at a temperature of up to 200° C. This polymorph is unstable in the presence of atmospheric moisture, forming variable hydrates.

Techniques for Analysis of Forms A, B, C and Amorphous Material

X-Ray Powder Diffraction

X-ray powder diffraction (XRPD) analyses were carried out on a Shimadzu XRD-6000 X-ray powder diffractometer using Cu Kα radiation. The instrument was equipped with a fine focus X-ray tube, and the tube voltage and amperage were set to 40 kV and 40 mA respectively. The divergence and scattering slits were set at 1" and the receiving slit was set at 0.15 mm. Diffracted radiation was detected by a NaI scintillation detector. A theta-two theta continuous scan at 3°/min (0.4 sec/0.02° step) from 2.5-40° 2θ was used. A silicon standard was used to check the instrument alignment. Data were collected and analyzed using XRD-6000 v. 4.1 software.

X-ray powder diffraction (XRPD) analyses were also performed using an Inel XRG-3000 diffractometer equipped with a CPS (Curved Position Sensitive) detector with a 2θ range of 120°. The instrument calibration was performed using a silicon reference standard. The tube voltage and amperage were set to 40 kV and 30 mA, respectively. The monochromator slit was set at 5 mm by 80 μm. Samples were placed in an aluminum sample holder with a silicon insert or in glass XRPD-quality capillaries. Each capillary was mounted onto a goniometer head that is motorized to permit spinning of the capillary during data acquisition. Real time data were collected using Cu-Kα radiation at a resolution of 0.03° 2θ. Typically, data were collected over a period of 300 seconds. Only the data points within the range of 2.5-40° 2θ are displayed in the plotted XRPD patterns.

Thermal Analyses

Thermogravimetric (TG) analyses were carried out on a TA Instruments 2050 or 2950 thermogravimetric analyzer. The calibration standards were nickel and Alumel™. Samples were placed in an aluminum sample pan, inserted into the TG furnace, and accurately weighed. The samples were heated in nitrogen at a rate of 10° C./min to either 300 or 350° C. Unless stated otherwise, sample weights were equilibrated at 25° C. in the TGA furnace prior to analysis.

Differential scanning calorimetry (DSC) analyses were carried out on a TA Instruments differential scanning calorimeter 2920. Accurately weighed samples were placed in either crimped pans or hermetically sealed pans that contained a pinhole to allow for pressure release. Each sample was heated under nitrogen at a rate of 10° C./min to either 300 or 350° C. Indium metal was used as the calibration standard. Temperatures were reported at the transition maxima.

Infrared Spectroscopy

Infrared spectra were acquired on Magna 860® Fourier transform infrared (FT-IR) spectrophotometer (Nicolet Instrument Corp.) equipped with an Ever-Glo mid/far IR source, an extended range potassium bromide beamsplitter, and a deuterated triglycine sulfate (DTGS) detector. Unless stated otherwise, a Spectra-Tech, Inc. diffuse reflectance accessory (the Collector™) was used for sampling. Each spectrum represents 256 co-added scans at a spectral resolution of 4 cm$^{-1}$. Sample preparation for the compound consisted of placing the sample into a microcap and leveling the material with a frosted glass slide. A background data set was acquired with an alignment mirror in place. The spectra represent a ratio of the sample single-beam data set to the background single beam data set. Wavelength calibration of the instrument was performed using polystyrene.

NMR Spectroscopy

Solution phase $^1$H NMR spectra of the were acquired at ambient temperature on a Bruker model AM-250 spectrometer operating at 5.87 T (Larmor frequency: $^1$H=250 MHz). Time-domain data were acquired using a pulse width of 7.5 ps and an acquisition time of 1.6834 second over a spectral window of 5000 Hz. A total of 16,384 data points were collected. A relaxation delay time of 5 seconds was employed between transients. Each data set typically consisted of 128 coaveraged transients. The spectra were processed utilizing GRAMS132 A1 software, version 6.00. The free induction decay (FID) was zero-filled to four times the number of data points and exponentially multiplied with a line-broadening factor of 0.61 Hz prior to Fourier transformation. The $^1$H spectra were internally referenced to tetramethylsilane (0 ppm) that was added as an internal standard.

Alternatively, NMR analysis was carried out as described in Example 4.

Moisture Sorption/Desorption Analyses

Moisture sorption/desorption data were collected on a VTI SGA-100 Vapor Sorption Analyzer. Sorption and desorption data were collected over a range of 5% to 95% relative humidity (RK) at 10% RH intervals under a nitrogen purge. Sodium chloride (NaCl) and polyvinylpyrrolidone (PVP) were used as the calibration standards. Equilibrium criteria used for analysis were less than 0.0100% weight change in 5 minutes, with a maximum equilibration time of 180 minutes if the weight criterion was not met. The plotted data have not been corrected for the initial moisture content.

Nomenclature

The structure of the compound (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide is as follows:

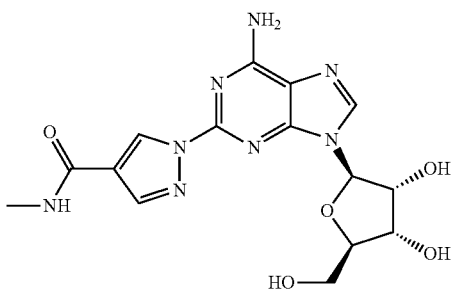

Synthesis of (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide One method for the large scale synthesis of (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide is shown in Reaction Scheme I. All reactions are typically preformed under a nitrogen atmosphere.

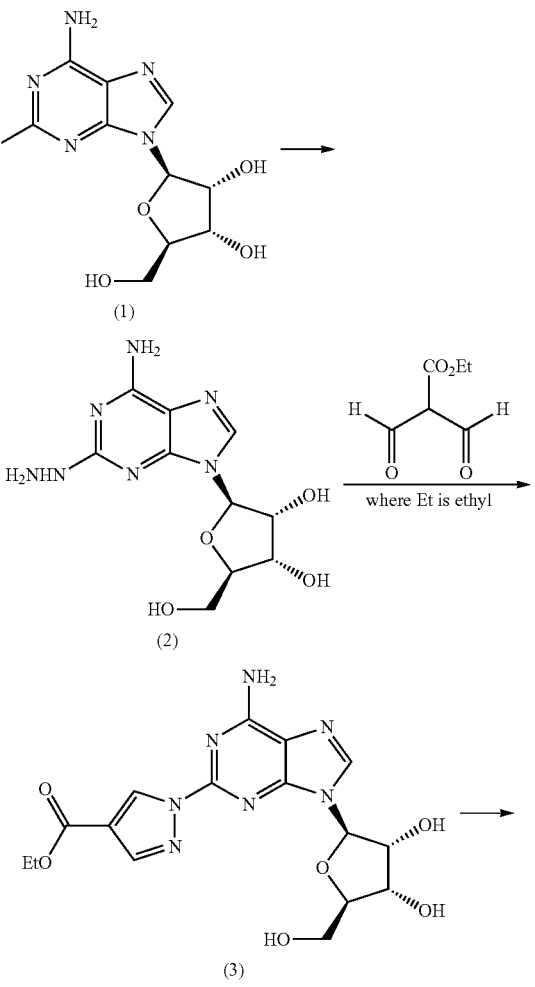

-continued

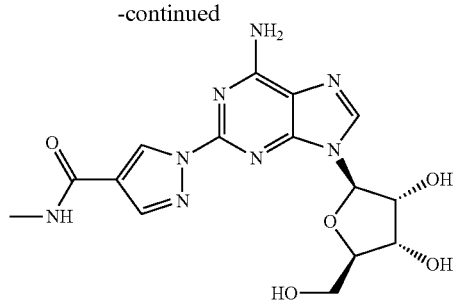

Step 1—Preparation of Formula (2)

The compound of formula (2) is prepared from the compound of formula (1) by reaction with hydrazine monohydrate in the absence of a solvent. The reaction is conducted at a temperature of about 45-55° C. When the reaction is complete, the product of formula (2) is isolated by stirring with a protic solvent in which the compound of formula (2) has limited solubility, for example ethanol or isopropanol. The mixture is stirred for about 1-5 hours, and then filtered. The solid is purified by stirring with water, filtering, and washing with water followed by isopropanol and dried under vacuum, which is taken to the next step without purification.

Step 2—Preparation of Formula (3)

The compound of formula (2) is then converted to a compound of formula (3) by reacting with about 1-1.2 molar equivalents of ethyl 2-formyl-3-oxopropionate. The reaction is conducted in a protic solvent, preferably ethanol, at about reflux temperature, for about 2-4 hours. After cooling, to about 0° C., the solid is filtered off, washed with cold ethanol, and dried under reduced pressure. The product of formula (3) is taken to the next step without purification.

Step 3—Preparation of Final Product

The final product is prepared from the compound of formula (3) by reacting with methylamine, preferably aqueous methylamine. The reaction is carried out at about room temperature, for about 4 hours. The product of Formula I is isolated by conventional means, for example by filtration, washing the solid with cold ethanol, and drying under reduced pressure.

Preparation of Starting Materials (4S,2R,3R,5R)-2-(6-amino-2-chloropurin-9-yl)-5-(hydroxymethyl)oxolane-3,4-diol is used as a starting material in step 1. This compound is commercially available.

Ethyl 2-formyl-3-oxopropanoate is used as a starting material in step 2. It is commercially available, or may be made as shown in Reaction Scheme II.

REACTION SCHEME II

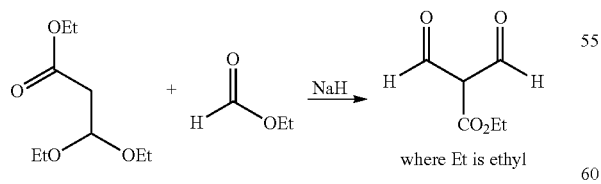

Ethyl 3,3-diethoxypropionate is reacted with ethyl formate in the presence of a strong base, preferably sodium hydride. The reaction is carried out at about 0-5° C., for about 24 hours. The product is isolated by conventional means, for example by the addition of water and extraction of impurities with a conventional solvent, for example t-butylmethyl ether, acidification of the aqueous phase with, for example, hydrochloric acid, followed by extraction with a solvent such as dichloromethane, and removing the solvent from the dried extract under reduced pressure. Ethyl 2-formyl-3-oxopropanoate is purified by distillation under reduced pressure.

A preferred method for the large scale synthesis of (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide is shown in Reaction Scheme III.

REACTION SCHEME III

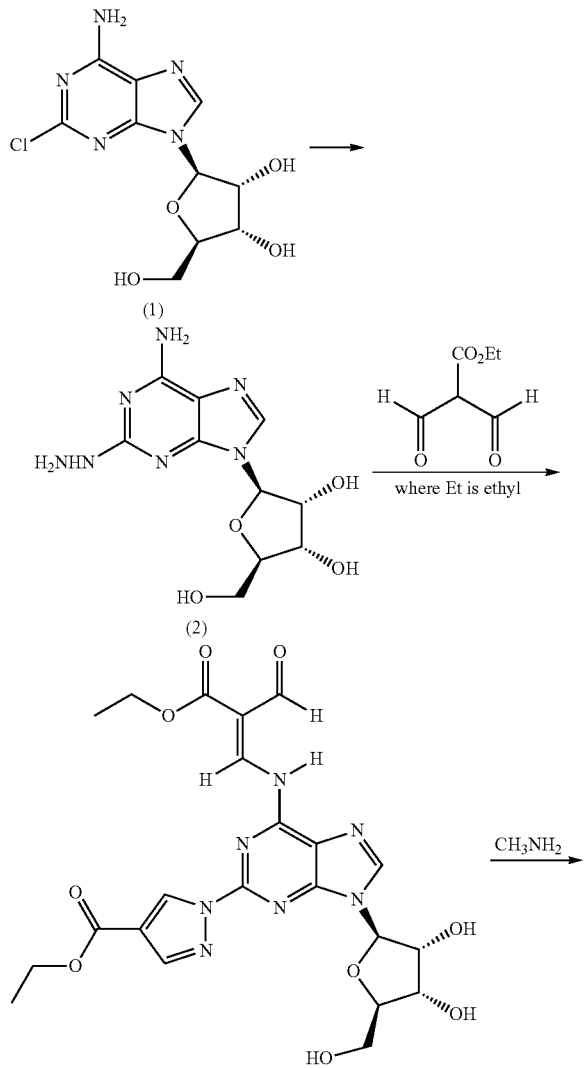

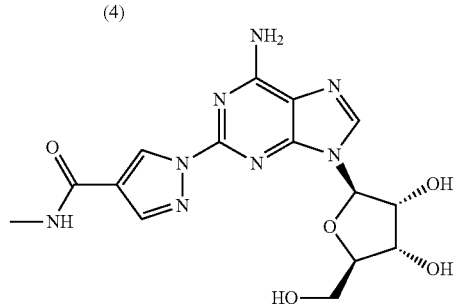

Step 1—Preparation of Formula (2)

As before, the compound of formula (2) is prepared from the compound of formula (1) by reaction with hydrazine monohydrate in the absence of a solvent. In this method however, a 14.3-16.7 fold molar excess of hydrazine monohydrate is first heated to approximately 60-65° C. followed by addition of the compound of formula (1). The temperature is maintained at approximately 60-65° C. during the reaction which takes approximately 1 to 3 hours to complete. When the level of residual compound of formula (1) in the mixture is not more than approximately 0.10%, the reaction mixture is then cooled to approximately 40° C. The temperature is maintained while water is slowly added. Once approximately 4.2-4.9 mass equivalence have been added, the mixture is cooled to approximately 10° C. and held at that temperature for not less than 1 hour.

The product is then isolated by filtration, washed with water, and then washed with absolute ethanol. The solid is dried under vacuum at up to 30° C. for not less than 12 hours and then taken to the next step without further purification.

Step 2—Preparation of Formula (4)

The compound of formula (2) is then converted to a compound of formula (4) by reacting with an excess of ethyl 2-formyl-3-oxopropionate, for example a 2-10 fold excess, preferably about 5-10 fold, ideally about 6.8-7.5 fold excess. The reaction may be conducted under the same conditions as those described for the preparation of the compound of formula (3) in Reaction Scheme I.

Alternatively, approximately 0.05 molar equivalents of an acid such as HCl may also be added to the reaction mixture. The reaction is allowed to proceed at reflux temperature, for about 2-4 hours, until the level of residual compound of formula (2) is not more that 0.50% and the amount of any compound of formula (3) that may have formed is not more than 2.5%. After cooling, to about 10° C., the solid is filtered off, washed with absolute ethanol, and dried under vacuum at up to 40° C. to remove residual ethanol. The product of formula (4) is taken to the next step without purification.

The compound of formula (4) is drawn as a (2E) alkene derivative, as this is the major isomer formed in this reaction. However, it should be noted that a significant amount of the (2Z) alkene derivative may also be formed in this reaction; that is:

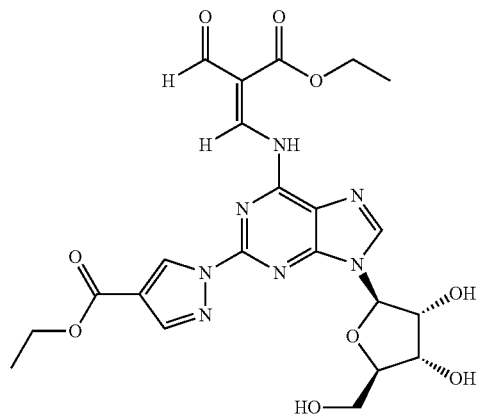

named as ethyl (2Z)-3-({9-[(4S,2R,3R,5R)-3,4-dihydroxy-5-(hydroxymethyl)-oxolan-2-yl]-2-[4-(ethoxycarbonyl) pyrazolyl]purin-6-yl}amino)-2-formylprop-2-enoate.

Accordingly, although the compound of formula (4) is represented as the (2E) alkene derivative only, the term "compound of formula (4)" is intended to include both the instance where it is solely the (2E) isomer, and the instance where the major portion of the product is the (2E) isomer and a minor portion of the (2Z) isomer is also present. The conversion of the compound of formula (4) to the final product by reaction with methylamine as described in Step 3 proceeds in the same manner whether the compound of formula (4) is present as the (2E) isomer or as a mixture of the (2E) isomer and the (2Z) isomer.

Step 3—Preparation of Final Product

The final product is prepared from the compound of formula (4) by reacting with methylamine, preferably aqueous methylamine. The reaction is initially carried out at about 0-5° C. for about 8 hours, preferably in a pressure reactor, followed by raising the temperature to 50-60° C. over about 1 hour, and maintaining the temperature for 15-30 minutes.

Alternatively, the methylamine is first placed into the pressure vessel and cooled to approximately 2.5-7.5° C. and then the compound of formula (4) is added while the temperature is maintained. The reaction proceeds until the level of residual compound of formula (3) is less than approximately 0.10%.

Upon completion, the product is isolated by conventional means, for example by degassing under vacuum at not more than approximately 35° C. to remove excess methylamine. The vacuum is then released and the mixture cooled to approximately 0-5° C. and held at the temperature for 15 minutes to an hour, followed by filtration. The solid thus obtained is washed with water followed by ethanol, and dried under reduced pressure at a temperature of no more than approximately 40° C.

This process provides (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide as its monohydrate. This polymorph can be further purified by dissolving in dimethylsulfoxide (DMSO), filtering any solid impurities from the solution, rinsing with additional DMSO, and precipitating the monohydrate from solution by addition to water. This method is particularly effective when the DMSO solution and water are heated to approximately 78-88° C. and held at that temperature with stirring for approximately 1 hour. After stirring, the slurry is slowly cooled to approximately 20° C. The final product is then isolated by filtration, washed with purified water followed by ethanol, and dried as described previously.

EXAMPLE 1

Preparation of Ethyl-2-formyl-3-oxopropionate

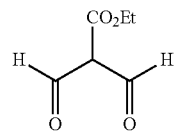

A three- or four-neck round bottom flask equipped with magnetic stir bar, thermocouple, digital thermometer, gas inlet and outlet and addition funnel was flushed with argon. Ethyl 3,3-diethoxypropionate (64.5 g) in tetrahydrofuran were charged to the addition funnel. Sodium hydride (21.2 g of a 60% dispersion) was charged to the reaction flask followed by tetrahydrofuran. The contents of the flask were cooled to 0-5° C. in an ice-bath, and ethyl formate (257 g) was added. The mixture was cooled to 0-5° C. and the contents of the addition funnel added dropwise, maintaining an internal temperature of less than 5° C. The ice-bath was removed and the contents allowed to warm to ambient temperature. Consumption of ethyl 3,3-diethoxypropionate was monitored by TLC analysis. The reaction was quenched by addition of ice-water (10.6 vol), and extracted three times with methyl t-butyl ether (5.4 vol each), and the organic layers discarded. The aqueous phase was acidified with conc. hydrochloric acid to a pH of 1 to 1.5. The acidified aqueous layer was extracted three times with dichloromethane and the combined organic layers dried over sodium sulfate. The solvent was removed under reduced pressure, and the residue distilled under vacuum, to provide ethyl 2-formyl-3-oxopropionate, 27.92 g, 70% yield.

EXAMPLE 2

A. Preparation of 2-Hydrazinoadenosine (2)

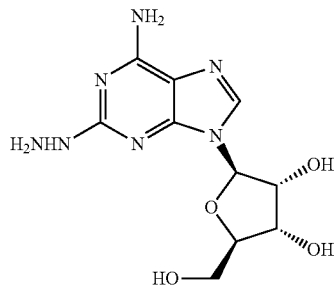

(2)

A flask equipped with a mechanical stirrer, gas inlet, gas outlet and thermocouple was flushed with argon. 2-Chloroadenosine hemihydrate (53.1 g) was added, followed by hydrazine monohydrate (134 g). The mixture was stirred while heating to 40-45° C. for 2 hours. The progress of the reaction was followed by TLC analysis. When the reaction was complete, the heat source was removed and ethanol (800 ml) was added. The mixture was stirred for 2 hours at ambient temperature, then the precipitate collected by filtration. The filter cake was washed with ethanol and dried under reduced pressure for 30 minutes. The solids were transferred to a clean flask equipped with a mechanical stirrer and water (300 ml) was added. The suspension was stirred at room temperature for 18 hours, and the solids isolated by filtration. The filter cake was washed with ice-cold water (300 ml) followed by a wash with ice-cold ethanol (300 ml). The solid was dried under reduced pressure to provide 2-hydrazinoadenosine (41.38 g, 81.4% yield, 99.3% purity).

B. Alternative Preparation of 2-Hydrazinoadenosine (2)

A reaction vessel containing hydrazine hydrate (258 g, 250 ml) was heated to 40-50° C. To the warm mixture 2-chloroadenosine hemihydrate (100 g) was added in portions, maintaining the temperature between 45-55° C. The temperature was kept at this temperature for two hours, and then deionized water (500 ml) was added over a period of 30 minutes, maintaining the temperature at 45-55° C. The mixture was then gradually cooled to 0-5° C. over a period of 3 hours, then stirred at this temperature for a further 30 minutes. The solid was then filtered off, and washed with cold (2-5° C.) deionized water (200 ml), followed by ethanol (400 ml). The solid was dried under vacuum for 12 hours, to provide 2-hydrazinoadenosine.

C. Alternative Preparation of 2-Hydrazinoadenosine (2)

A reaction vessel is charged with hydrazine hydrate (1285 g). The solution is heated to approximately 62° C., and 2-chloroadenosine (500 g) is added while maintaining the temperature of approximately 62° C. The mixture is maintained at a target of 62° C. for at least 2 hours, until the level of residual 2-chloroadenosine in the mixture is not more than 0.10%. The mixture is cooled to approximately 40° C. and the mixture is checked to verify the presence of solids. Water (2275 g) is slowly added while maintaining the temperature at approximately 40° C. The mixture is cooled to approximately 10° C. and held for not less than 1 hour. The product is isolated by filtration, washed with water (1195 g) and then with absolute ethanol (1885 g). The product is dried under vacuum at up to 30° C. for not less than 12 hours, to give 2-hydrazinoadenosine.

EXAMPLE 3

Preparation of Ethyl 1-{9-[(4S,2R,3R,5R)-3,4-dihydroxy-5-(hydroxymethyl)oxolan-2-yl]-6-aminopurin-2-yl}pyrazole-4-carboxylate (3)

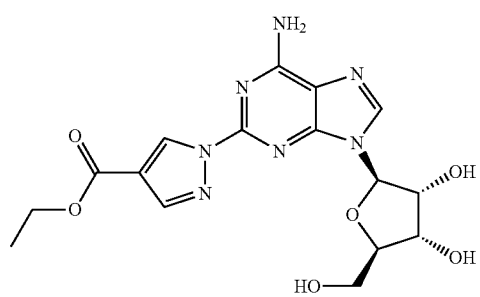

(3)

Ethyl 2-formyl-3-oxopropionate (23.93 g, 0.17 mol) was placed in a flask equipped with mechanical stirrer, gas inlet, gas outlet and reflux condenser. 2-Propanol was added to the flask followed by 2-hydrazinoadenosine (44.45 g, 0.15 mol). The mixture was heated to reflux under stirring for 2-4 hours, following the progress of the reaction by TLC analysis. When the reaction was judged complete, the heat source was removed and the mixture cooled to room temperature. The suspension was cooled under stirring in an ice-bath for 1.5 to 2 hours. The solids were isolated by vacuum filtration, and washed with ice-cold 2-propanol. The product, ethyl 1-{9-[(4S,2R,3R,5R)-3,4-dihydroxy-5-(hydroxymethyl)oxolan- 2-yl]-6-aminopurin-2-yl}pyrazole-4-carboxylate, was dried under reduced pressure to a constant weight.

EXAMPLE 4

Preparation of (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide

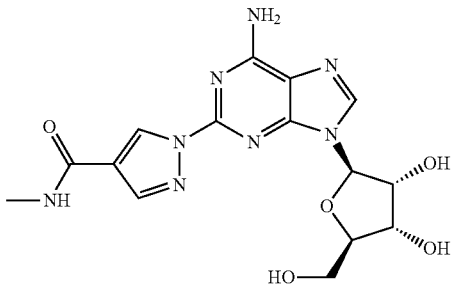

A mixture of ethyl 1-{9-[(4S,2R,3R,5R)-3,4-dihydroxy-5-(hydroxymethyl)oxolan-2-yl]-6-aminopurin-2-yl}pyrazole-4-carboxylate (46.4 g) and methylamine (40% in water, 600 ml) was stirred at ambient temperature for about 4 hours, following the progress of the reaction by HPLC analysis. The majority of the excess methylamine was removed under reduced pressure, and the remaining mixture cooled at 0° C. for 2 hours. The solid material was filtered off, washed with ice-cold 200 proof ethanol, and dried under reduced pressure, to provide (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide as its monohydrate.

Figure 1:
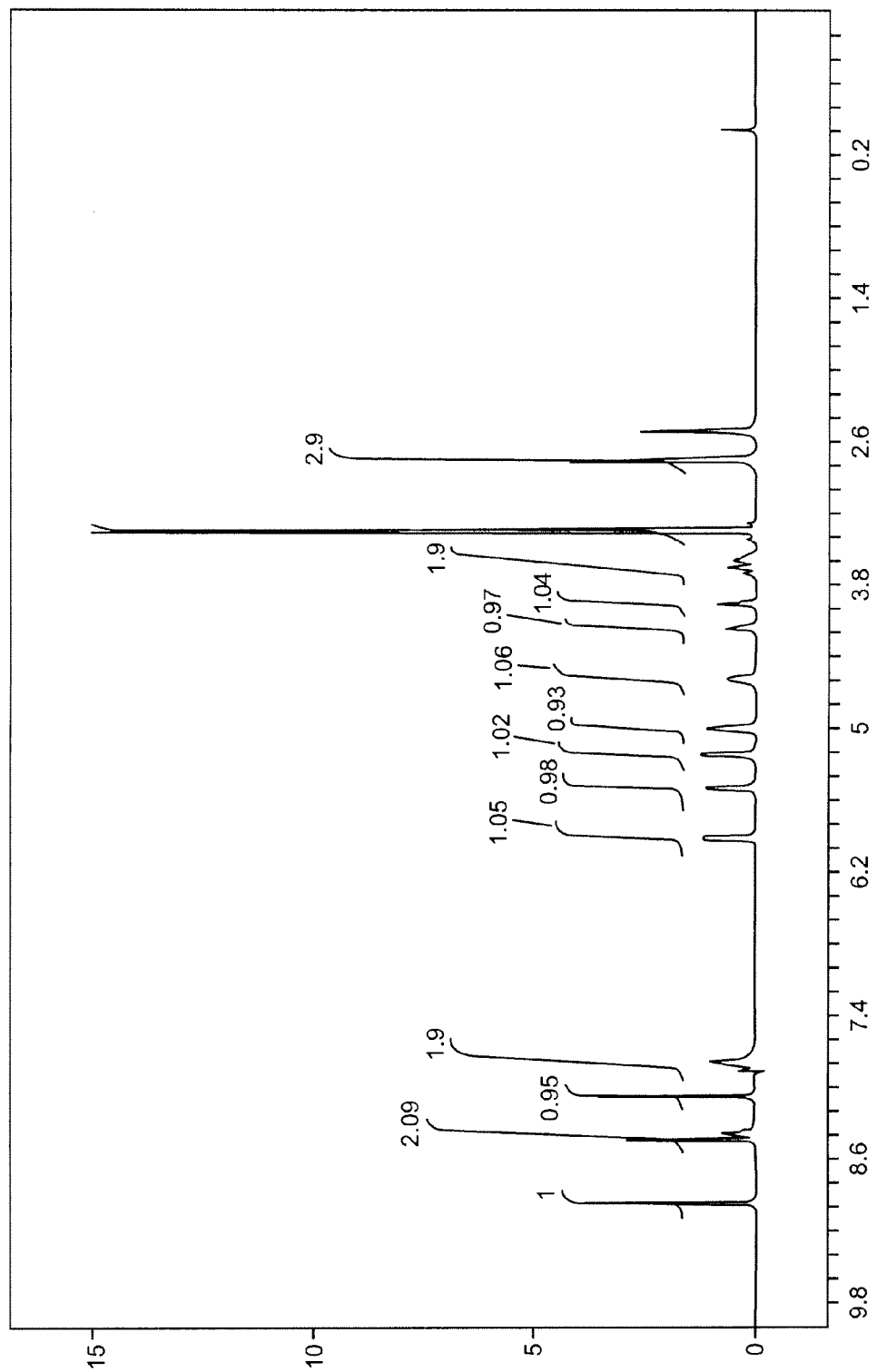
FIG. 1 is a $^1$H NMR spectrum of (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide monohydrate (Form A).
Figure 2:
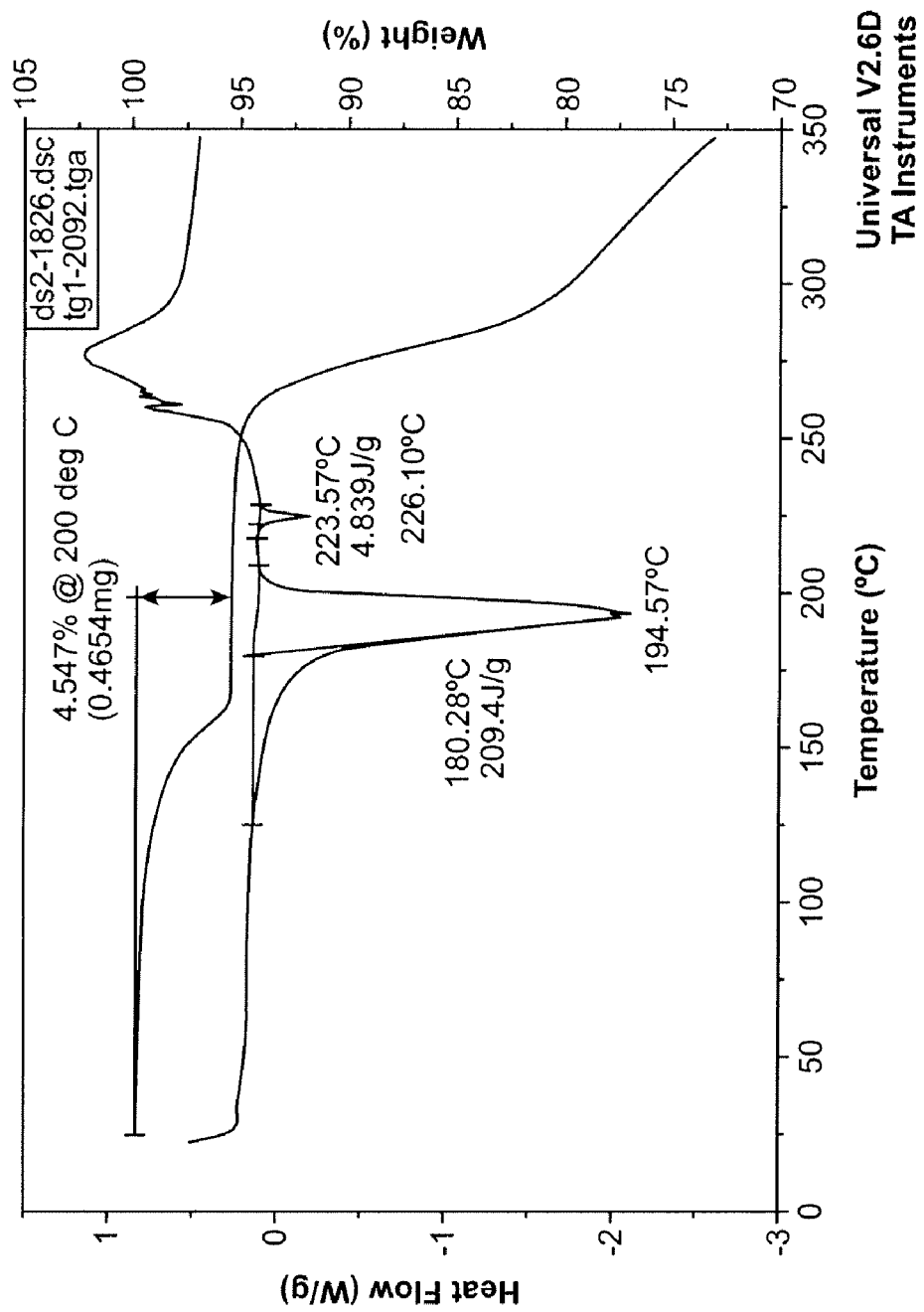
FIG. 2 shows the thermal analysis of (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide monohydrate.
Figure 3:
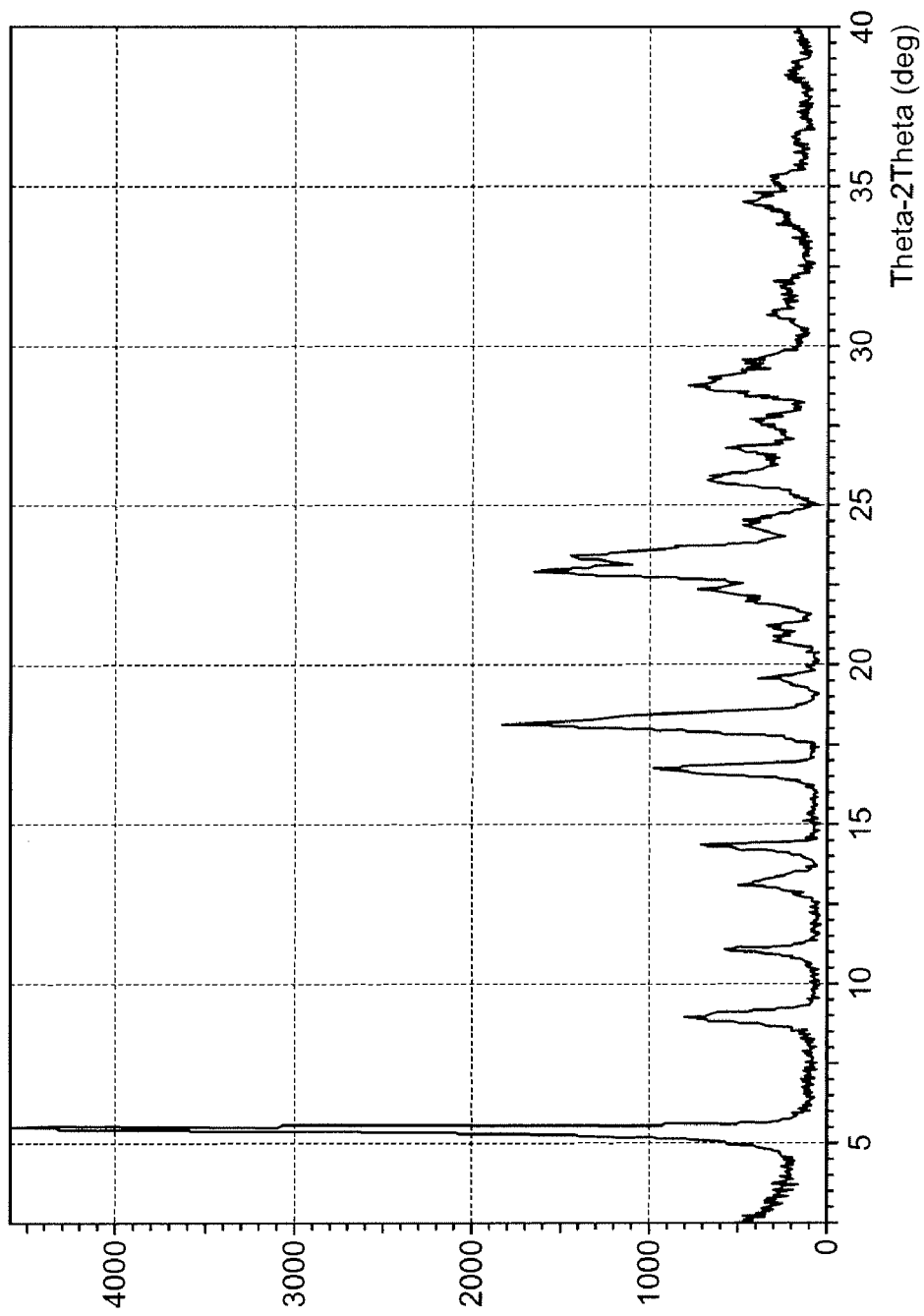
FIG. 3 shows the X-Ray diffraction pattern for (1-{9-[(4S,2R,3R,5R)-3,4-dihydroxy-5-(hydroxymethypoxolan-2-yl]-6-aminopurin-2-yl}pyrazol-4-yl)-N-methylcarboxamide monohydrate.

The structure of the material was confirmed by $^1$H NMR (see FIG. 1 and below). Thermal analysis (see FIG. 2) provided results consistent with the presence of one molecule of water. X-Ray powder diffraction patterns were obtained (FIG. 3)

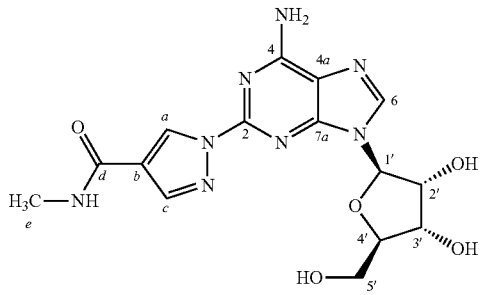

$^1$H and $^{13}$C NMR spectra were obtained in the following manner. Two samples of the material obtained above were weighed out and dissolved in $d_6$-DMSO—5.3 mg was used for the $^1$H spectra, and 20.8 mg was used for $^{13}$C spectra. All spectra were acquired at ambient temperature on a JEOL Eclipse$^+$ 400 spectrometer operating at 400 MHz for $^1$H and 100 MHz for $^{13}$C.

| Label | $^{13}$C shift(ppm) | $^1$H shift(ppm) | Multiplicity, splitting(Hz) |
|---|---|---|---|
| 2 | 150.5 or 150.3 | — | |
| 4 | 156.4 | — | |
| 4a | 117.9 | — | |
| 6 | 140.0 | 8.41 | s |
| 7a | 150.5 or 150.3 | — | |
| 1' | 86.9 | 5.94 | D, 6.2 |
| 2' | 73.7 | 4.62 | m |
| 2'-OH | — | 5.50 | D, 6.2 |
| 3' | 70.5 | 4.17 | m |
| 3'-OH | — | 5.23 | D, 4.7 |
| 4' | 85.7 | 3.96 | m |
| 5' | 61.5 | 3.67, 3.57 | m |
| 5'-OH | — | 5.02 | D, 5.7 |
| A | 140.9 | 8.07 | D, 0.8 |
| B | 120.2 | — | |
| C | 129.6 | 8.95 | D, 0.8 |
| D | 161.7 | — | |
| E | 25.6 | 2.76 | D, 4.6 |
| NH$_2$ | — | 7.77 | br s |
| NH | — | 8.35 | Q, 4.6 |

EXAMPLE 5

A. Preparation of Ethyl (2E)-3-({9-[(4S,2R,3R,5R)-3,4-dihydroxy-5-(hydroxymethyl)-oxolan-2-yl]-2-[4-(ethoxycarbonyl)pyrazolyl]purin-6-yl}amino)-2-formylprop-2-enoate (4)

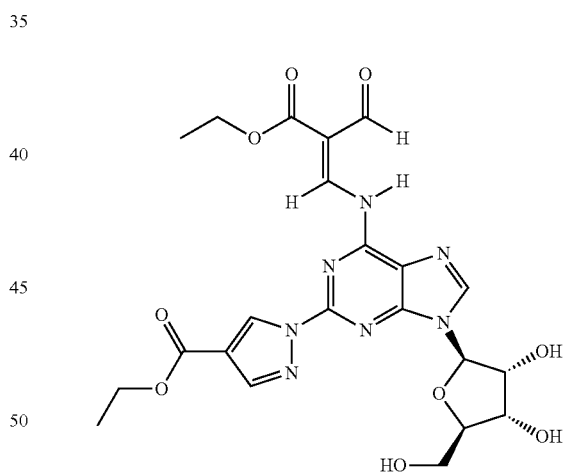

A mixture of 2-hydrazinoadenosine (100 g, 0.34 mol), ethyl 2-formyl-3-oxopropionate (242 g, 1.7 mol) and absolute ethanol were charged to a reactor, and the mixture heated to reflux for 2 hours. When the reaction was judged complete, the heat source was removed and the mixture gradually cooled to 5-10° C. over a period of 3 hours. The slurry was stirred for 30 minutes at this temperature, and the mixture filtered. The solid material was washed with cold (5-10° C.) absolute ethanol, and then dried under vacuum at a temperature that did not exceed 40° C., to provide ethyl (2E)-3-({9-[(4S,2R,3R,5R)-3,4-dihydroxy-5-(hydroxymethyl)oxolan-2-yl]-2-[4-(ethoxycarbonyl)-pyrazolyl]purin-6-yl}amino)-2-formylprop-2-enoate.

B. Alternative Preparation of Ethyl (2E)-3-({9-[(4S,2R,3R,5R)-3,4-dihydroxy-5-(hydroxymethyl)-oxolan-2-yl]-2-[4-(ethoxycarbonyl)pyrazolyl]purin-6-yl}amino)-2-formylprop-2-enoate (4)

A reaction vessel is charged with 2-hydrazinoadenosine (450 g) and absolute ethanol (11376 g). HCl (7.47 g) and ethyl 2-formyl-3-oxopropionate (1557 g) are added. The mixture is heated to reflux and sampled until the level of residual 2-hydrazinoadenosine in the mixture is not more than 0.50% and the level of the compound of formula (3) is not more than 2.5%. The mixture is slowly cooled to approximately 10° C. The product, the compound of formula (4) is isolated by filtration and washed with absolute ethanol (5121 g). The product is dried under vacuum at up to 40° C. until residual ethanol is not more than 5000 ppm to give ethyl (2E)-3-({9-[(4S,2R,3R,5R)-3,4-dihydroxy-5-(hydroxymethyl)oxolan-2-yl]-2-[4-(ethoxycarbonyl)-pyrazolyl]purin-6-yl}amino)-2-formylprop-2-enoate.

An elemental analysis of the product of Example 5A gave the following results: C, 48.75%; H, 4.86%; N, 18.05%; O, 27.57. Theoretical: C, 49.72%; H, 4.74%; N, 18.45%; O, 27.09. The analysis corresponds within experimental error limits to the hemihydrate of the desired product. (C, 48.89%; H, 4.81%; N, 18.1%; O, 28.12)

$^1$H and $^{13}$C NMR spectra were obtained in the following manner. 20.2 mg of the compound of formula (4) was dissolved in ~0.75 ml of DMSO-d6, and the spectra obtained at ambient temperature on a JEOL ECX-400 NMR spectrometer operating at 400 MHz for $^1$H and 100 MHz for $^{13}$C. The chemical shifts were referenced to the DMSO solvent, 2.50 ppm for $^1$H and 39.5 ppm for $^{13}$C.

Results

The $^1$H and $^{13}$C chemical shifts are listed in Table 1. Two isomers in a ratio of ~60/30 were observed in both the $^1$H and the $^{13}$C spectra, labeled as major and minor in the table.

| Atom[a] | $^{13}$C Chemical Shift (ppm) | $^1$H Chemical Shift (ppm) | Multiplicity[b], Splitting (Hz) |
|---|---|---|---|
| 21(major) | 192.4 | 9.96 | d, 3.6 |
| 21(minor) | 187.6 | 9.83 | s |
| 22(minor) | 167.1 | — | — |
| 22(major) | 165.2 | — | — |
| 15(minor) | 161.8 | — | — |
| 15(major) | 161.7 | — | — |
| 6(major) | 153.1 | — | — |
| 6(minor) | 152.9 | — | — |
| 2(minor) | 149.4 | — | — |
| 2(major) | 149.3 | — | — |
| 19(minor) | 148.0 | 9.22 | d, 13.0 |
| 4(minor) | 147.9 | — | — |
| 4(major) | 147.8 | — | — |
| 19(major) | 147.5 | 9.26 | d, 12.4, d, 3.6 |
| 8(major) | 144.9 | 8.87 | s |
| 8(minor) | 144.7 | 8.85 | s |
| 12 | 143.1 | 8.20-8.23 | m |
| 14(minor) | 132.8 | 9.20 | d, ~0.7 |
| 14(major) | 132.6 | 9.12 | d, ~0.7 |
| 5(major) | 120.7 | — | — |
| 5(minor) | 120.6 | — | — |
| 13 | 116.7 | — | — |
| 20(minor) | 107.2 | — | — |
| 20(major) | 106.1 | — | — |
| 1'(major) | 87.9 | 6.07 | d, 5.3 |
| 1'(minor) | 87.9 | 6.06 | d, 5.3 |
| 4' | 85.8 | 4.02 | q, 3.9 |
| 2'(minor) | 74.1 | 4.62 | q, ~5.4 |
| 2'(major) | 74.1 | 4.61 | q, ~5.4 |
| 3' | 70.1 | 4.22 | q, 4.2 |
| 5' | 61.0 | 3.62, 3.73 | m |
| 23, 16 | 60.3-60.8 | 4.25-4.39 | m |
| 17, 24 | 14.1-14.2 | 1.28-1.38 | m |
| 18(major) | — | 12.51 | d, 12.4 |
| 18(minor) | — | 11.47 | d, 13.0 |
| 2'-OH (major) | — | 5.63 | d, 6.1 |
| 2'-OH (minor) | — | 5.62 | d, 6.1 |
| 3'-OH | — | 5.30 | d, 5.1 |
| 5'-OH | — | 5.08 | t, 5.5 |

The compound of formula (4) was confirmed to be a mixture of the following two isomers:

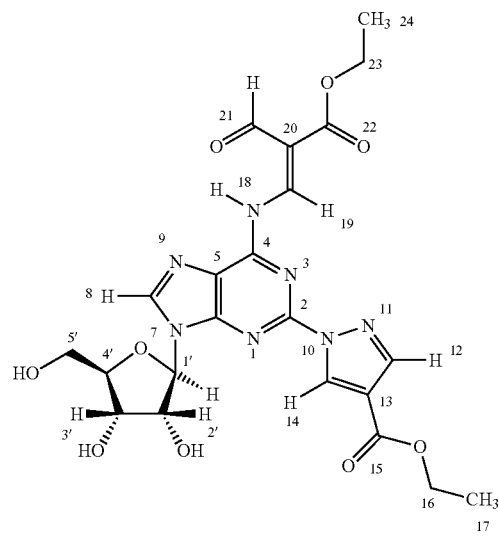

Major

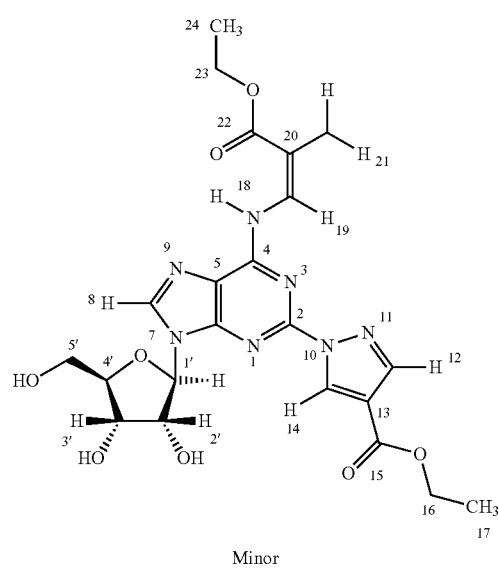

Minor

EXAMPLE 6

A. Preparation of (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide from Compound (4)

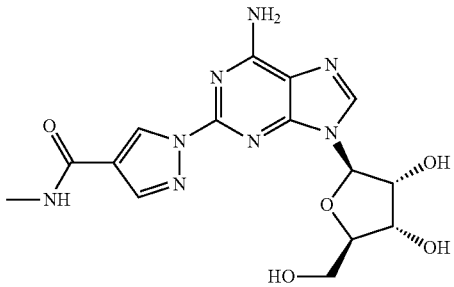

Aqueous 40% methylamine solution (1300 ml) was placed in a pressure reactor, cooled to 0-5° C., and the product of Example 5A (ethyl (2E)-3-({9-[(4S,2R,3R,5R)-3,4-dihydroxy-5-(hydroxymethyl)oxolan-2-yl]-2-[4-(ethoxycarbonyl)pyrazolyl]purin-6-yl}amino)-2-formylprop-2-enoate (100 g) added. The mixture was stirred at 0-5° C. for at least 8 hours, monitoring the reaction for completion. When complete, the mixture was warmed, maintaining the temperature between 50 and 60° C. for 1 hour, and then cooled to less than 30° C. over a period of 1 hour. When the temperature was below 30° C., the mixture was degassed using a pressure of 100-150 mm Hg, allowing the temperature to decrease to 0-5° C. The mixture was stirred at 0-5° C. for at least 1 hour, maintaining the pressure at 100-150 mm Hg. The vacuum was then discontinued and replaced by nitrogen, maintaining the temperature at 0-5° C. for not less than 30 minutes. The solid product was then filtered off, washed with water (3×500 ml), then with absolute ethanol (625 ml). The product was dried under vacuum, not allowing the temperature to exceed 40° C., to provide (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide as its monohydrate.

B. Alternative Preparation of (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide from Compound (4)

A pressure vessel is charged with 47% methylamine solution (10080 g). The solution is cooled and the compound of formula (4) as prepared in Example 5B above (600 g) is added while maintaining a target temperature of 5° C. The mixture is stirred at a target temperature of 5° C. until the level of residual compound of formula (3) in the mixture is less than 0.10%. The reaction mixture is degassed under vacuum at not more than 35° C. to remove excess methylamine. The vacuum is released and the mixture is cooled to 2.5° C. and held for at least 30 min. The product is then isolated by filtration, washed with water (not less than 9000 g) and then with absolute ethanol (not less than 2964 g). The product is dried under vacuum at up to 40° C. until the residual ethanol is not more than 5000 ppm to give crude (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide as its monohydrate.

$^1$H and $^{13}$C NMR spectra were obtained in the following manner. Two samples of the material obtained in Example 6A were weighed out and dissolved in $d_6$-DMSO—5.3 mg was used for the $^1$H spectra, and 20.8 mg was used for $^{13}$C spectra. All spectra were acquired at ambient temperature on a JEOL Eclipse$^+$ 400 spectrometer operating at 400 MHz for $^1$H and 100 MHz for $^{13}$C.

| Label | $^{13}$C shift(ppm) | $^1$H shift(ppm) | Multiplicity, splitting(Hz) |
|---|---|---|---|
| 2 | 150.5 or 150.3 | — | |
| 4 | 156.4 | — | |
| 4a | 117.9 | — | |
| 6 | 140.0 | 8.41 | s |
| 7a | 150.5 or 150.3 | — | |
| 1' | 86.9 | 5.94 | D, 6.2 |
| 2' | 73.7 | 4.62 | m |
| 2'-OH | — | 5.50 | D, 6.2 |
| 3' | 70.5 | 4.17 | m |
| 3'-OH | — | 5.23 | D, 4.7 |
| 4' | 85.7 | 3.96 | m |
| 5' | 61.5 | 3.67, 3.57 | m |
| 5'-OH | — | 5.02 | D, 5.7 |
| A | 140.9 | 8.07 | D, 0.8 |
| B | 120.2 | — | |
| C | 129.6 | 8.95 | D, 0.8 |
| D | 161.7 | — | |
| E | 25.6 | 2.76 | D, 4.6 |
| NH$_2$ | — | 7.77 | br s |
| NH | — | 8.35 | Q, 4.6 |

An elemental analysis gave the following results: C, 43.96%; H, 4.94%; N, 27.94. Theoretical: C, 44.12%; H, 4.94%; N, 27.44%; O, 27.09. The analysis corresponds within experimental error limits to the monohydrate.

EXAMPLE 7

A. Purification of (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide monohydrate A solution of (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide monohydrate, as prepared in Example 4, (100 g) in dimethylsulfoxide (300 ml) was filtered through a 0.6 to 0.8 micron prefilter and a 0.2 micron filter to remove any solid impurities. The filtrate was then slowly added over a period of 1 hour to deionized water (1 liter) with stirring, and the slurry thus produced stirred for not less than 1 hour. The solid was filtered off, washed with deionized water (2×1 liter), and dried under vacuum for not less than 1 hour.

The dried product was then slurried again with deionized water (1.5 liter) for not less than 2 hours, filtered off, and washed with deionized water (1 liter) followed by absolute ethanol (750 ml). The purified product was dried under vacuum at a temperature of not more than 40° C. for not less than 12 hours, to provide (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide monohydrate free of any 2-hydrazinoadenosine impurity.

B. Alternative Purification of (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide monohydrate A solution of (1-{9-[(4S,2R,3R,5R)-3,4-dihydroxy-5-(hydroxymethyl)oxolan-2-yl]-6-aminopurin-2-yl}pyrazol-4- yl)-N-methylcarboxamide monohydrate, (400 g) is dissolved in DMSO (1320 g), and the solution is filtered through 0.6 to 0.8-micron and 0.2-micron in-line filters in series. Additional DMSO (880 g) is used to rinse the filter system. The solution is slowly added to purified water (5000 g) while maintaining a target temperature of 83° C. The product begins to crystallize during the addition, and the slurry is stirred at a target of 83° C. for about 1 h. The mixture is slowly cooled to 20° C. The product is isolated by filtration and washed with purified water (8000 g).

The solids are charged to a vessel, and purified water (6000 g) is added. The slurry is mixed for about 1 hour. The product is isolated by filtration and washed with purified water (4000 g) and then with absolute ethanol (3160 g). The product is dried under vacuum at up to 40° C. until the residual water content is not more than 5.5% and the residual ethanol is not more than 2000 ppm to give (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide monohydrate.

We claim:

1. A method of synthesizing Compound A having the formula:

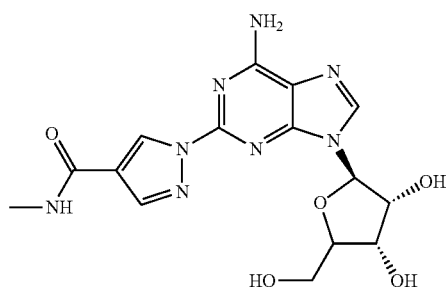

A comprising:
(a) contacting compound 1 having the formula:

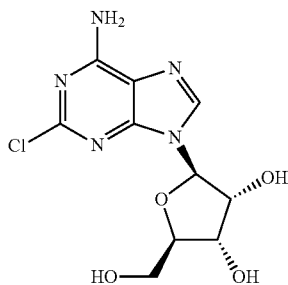

1 with a 14.3-16.7 fold molar excess of hydrazine to provide compound 2 having the formula:

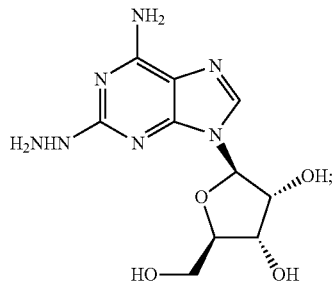

2

(b) contacting compound 2 with an excess of ethyl 2-formyl-3-oxopropionate to provide compound 4 having the formula:

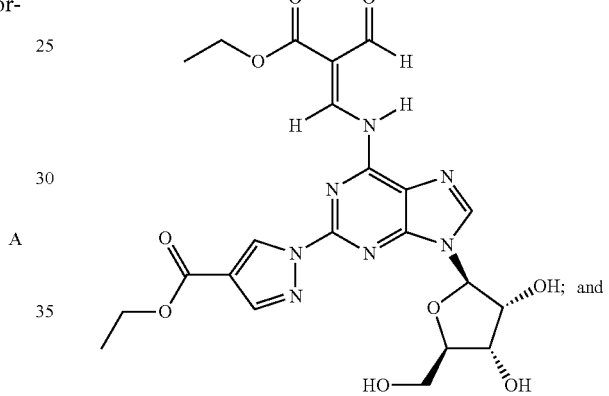

4

(c) contacting compound 4 with methylamine.

2. The method of claim 1, further comprising wherein the hydrazine in (a) is first heated to approximately 60-65° C. followed by addition of compound 1.

3. The method of claim 1, further comprising wherein compound 2 is isolated by:
  cooling the reaction mixture to approximately 40° C.;
  adding a 4.2-4.9 mass equivalent of water while maintaining the temperature at approximately 40° C.; and
  cooling the mixture to approximately 10° C. and maintaining at that temperature for at least approximately 1 hour.

4. The method of claim 3, further comprising:
  filtering the isolated compound 2;
  washing the contents of the filter with water followed by ethanol; and
  drying the solid that remains under vacuum at a temperature that does not exceed 30° C. for at least 12 hours.

5. The method of claim 1, wherein the excess ethyl 2-formyl-3-oxoproionate is about a 5-10 fold molar excess.

6. The method of claim 1, wherein the excess ethyl 2-formyl-3-oxoproionate is about a 6.8-7.5 fold molar excess.

7. The method of claim 1, wherein (b) further comprises adding HCl as a catalyst.

8. The method of claim 7, wherein the HCl is added in an amount of about 0.1 equivalents or less.

9. The method of claim 7, wherein the HCl is added in an amount of about 0.05 equivalents.

10. The method of claim 1, further comprising wherein (b) is carried out at about 80° C. and further comprises ethanol as a solvent.

11. The method of claim 1, further comprising wherein compound 4 is isolated by
cooling the completed reaction mixture to approximately 10° C.;
filtering;
washing the contents of the filter with ethanol; and
drying the solid that remains under vacuum at a temperature that does not exceed 40° C.

12. The method of claim 1, further comprising wherein (c) is carried out at approximately 2.5-7.5° C.

13. The method of claim 1, further comprising wherein Compound A is isolated by
degassing under vacuum at not more than 35° C. to remove excess methylamine;
releasing the vacuum and cooling to 0-5° C. for approximately 15-minutes to an hour;
filtering the slurry formed;
washing the contents of the filter with water followed by ethanol; and
drying the solid that remains under vacuum at a temperature that does not exceed 40° C.

14. The method of claim 13, further comprising wherein the Compound A is further purified by
(i) dissolving the dried solid in a solvent;
(ii) filtering any solid impurities from the solution;
(iii) rinsing with additional solvent;
(iv) adding solution to purified water that is maintained at approximately 78-88° C. thereby forming a slurry;
(v) stirring the slurry;
(vi) cooling the slurry;
(vii) filtering;
(viii) washing the contents of the filter with water followed by ethanol; and
(ix) drying the solid that remains under vacuum at a temperature that does not exceed 40° C.

15. The method of claim 14, further comprising wherein the solvent used in (i) and (iii) comprises dimethylsulfoxide.

16. The method of claim 14, wherein the residual water content of the Compound A product is not more than 5.5% and the residual ethanol of the Compound A product is not more than 2000 ppm.

* * * * *

UNITED STATES PATENT AND TRADEMARK OFFICE
CERTIFICATE OF CORRECTION

Page 1 of 1

PATENT NO. : 8,268,988 B2
APPLICATION NO. : 13/092812
DATED : September 18, 2012
INVENTOR(S) : Zablocki et al.

It is certified that error appears in the above-identified patent and that said Letters Patent is hereby corrected as shown below:

Title Page, Item (75) Inventors, should read

-- (75) Inventors: Jeff Zablocki, Mountain View, CA (US);
Elfatih Elzein, Fremont, CA (US);
Robert Seemayer, Belmont, CA (US);
Travis Lemons, Los Altos Hills, CA (US) --.

Signed and Sealed this
Eighth Day of March, 2016

Michelle K. Lee
*Director of the United States Patent and Trademark Office*